United States Patent
Wu et al.

(10) Patent No.: US 8,962,919 B2
(45) Date of Patent: Feb. 24, 2015

(54) METHOD FOR ENHANCING THERMOTOLERANCE OF PLANT RELATING TO EXPORTIN1A AND GENETIC ENGINEERING APPLICATIONS THEREOF

(75) Inventors: Shaw-Jye Wu, New Taipei (TW); Lian-Chin Wang, Taichung (TW); Shin-Jye Wu, Kinmen County (TW); Ching-Hui Yeh, New Taipei (TW); Chun-An Lu, Taipei (TW)

(73) Assignee: National Central University, Taoyuan County (TW)

( * ) Notice: Subject to any disclaimer, the term of this patent is extended or adjusted under 35 U.S.C. 154(b) by 689 days.

(21) Appl. No.: 13/050,971

(22) Filed: Mar. 18, 2011

(65) Prior Publication Data

US 2012/0060237 A1 Mar. 8, 2012

(30) Foreign Application Priority Data

Sep. 7, 2010 (TW) ................................ 99130236 A

(51) Int. Cl.
*C12N 15/82* (2006.01)
(52) U.S. Cl.
CPC .................................. *C12N 15/8271* (2013.01)
USPC .......................................... 800/289; 800/278
(58) Field of Classification Search
None
See application file for complete search history.

(56) References Cited

U.S. PATENT DOCUMENTS

2002/0053097 A1* 5/2002 Lindquist et al. ............. 800/298
2006/0150283 A1* 7/2006 Alexandrov et al. ......... 800/288

OTHER PUBLICATIONS

Yoo et al, SIZ1, small ubiquitin-like modifier E3 ligase facilitates basal thermotolerance in Arabidopsis independent of salicylic acid, Plant Physiol. (2006) 142:1548-1558.*
Von Koskull-Doring, The diversity of plant heat stress transcription factors, Trends Plant Sci. (2007) 12:452-457.*
Haasen et al, Nuclear export of proteins in plants: AtXPO1 is the export receptor for leucine-rich nuclear export signals in *Arabidopsis thaliana*, The Plant J. (1999) 20:695-705.*
Blanvillain et al, Exportin1 genes are essential for development and function of the gametophytes in *Arabidopsis*, Genetics (2008) 180:1493-1500.*
Blanvillain R et al., Exportin1 genes are essential for development and function of the gametophytes in *Arabidopsis thaliana*. Genetics 180:1493-1500, Nov. 2008.
Merkle T., Nucleo-cytoplasmic partitioning of proteins in plants: implications for the regulation of environmental and developmental signalling. Curr Genet. Dec. 2003;44(5):231-260. Epub Oct. 2, 2003.
Schramm F et al., The heat stress transcription factor HsfA2 serves as a regulatory amplifier of a subset of genes in the heat stress response in *Arabidopsis*. Plant Mol Biol. Mar. 2006; 60(5):759-772.

* cited by examiner

*Primary Examiner* — Cathy Kingdon Worley
*Assistant Examiner* — Mykola Kovalenko
(74) *Attorney, Agent, or Firm* — CKC & Partners Co., Ltd.

(57) ABSTRACT

A method for providing thermotolerance of a plant and the genetic engineering applications thereof are disclosed. DNA fragment containing a gene encoding EXPORTIN1A is transferred into a plant cell to provide or enhance thermotolerance of the plant. The method can be applied in genetic engineering to select transgenic plant.

8 Claims, 6 Drawing Sheets

METHOD FOR ENHANCING THERMOTOLERANCE OF PLANT RELATING TO EXPORTIN1A AND GENETIC ENGINEERING APPLICATIONS THEREOF

RELATED APPLICATIONS

This application claims priority to Taiwan Application Serial Number 99130236, filed Sep. 7, 2010, which is herein incorporated by reference.

SEQUENCE LISTING

The sequence listing submitted via EFS, in compliance with 37 CFR §1.52(e)(5), is incorporated herein by reference. The sequence listing text file submitted via EFS contains the file "TWT01669US-rsequencelisting", created on Jul. 4, 2013, which is 40,976 bytes in size.

BACKGROUND

1. Field of Invention

The present disclosure relates to a method for providing thermotolerance of a plant. More particularly, the present disclosure relates to a method for providing basal thermotolerance of a transgenic plant and genetic engineering applications thereof.

2. Description of Related Art

In the suitable environment, the growth and reproduction of plants are improved. On the other hand, the environmental variation may affect and be harmful to the plant growth. The environmental stresses, such as water deprivation, flood, heat, cold, chemical, heavy metal, peroxides poisonings, etc., may be harmful to the plants. Since those environmental stresses affect the growth or even survival of plants, finding out the mechanism of stress responses of plants can improve crop varieties and increase the yield and quality of crop.

The current global climate change is unusually warming or cooling. For instance, the greenhouse effect creates a heat stress for plant growth, and results in ecological calamity and food shortage problems. Over the past years, the research of heat stress response of plants was focused on heat shock proteins (HSPs), a class of functionally related proteins whose expression increase when cells are exposed to elevated temperatures or other stress, to investigate the short-term heat stress response of the plants. Heat shock proteins have a chaperone function in protein refolding. If a plant is placed at a higher, but not a lethal temperature, the heat shock proteins play an important role in protein-protein interactions to assist the refolding of the heat-denatured proteins to their proper conformation or prevent undesired protein misfolding and aggregation. These mechanisms are essential for plant survival after undergoing the short-term and lethally heat stress.

However, there is no further investigation of long-term, continuously heat stress response of plants. The long-term stresses affect the growth of plants; hence finding out the mechanism of long-term heat stress responses of plants can contribute to improving crop varieties, and increasing the yield and quality of crop.

In general, there are two ways to give the thermotolerance of a plant to resist the heat stress. One is to screen a mutant plant with a naturally occurring thermotolerance mutation. The other is to express one or more thermotolerance-related protein in a plant by using molecular biotechnology.

SUMMARY

In one aspect of the present disclosure, a plant, plant cell, plant material or seed of a plant is disclosed. A recombinant vector construct is introduced into the plant, the plant cell, the plant material or the seed of the plant. The recombinant vector construct comprises a promoter and an isolated nucleic acid sequence operably linked to the promoter for expressing an exogenous XPO1A protein in the plant, the plant cell, the plant material or the seed of the plant. The isolated nucleic acid sequence encodes a XPO1A protein of SEQ ID NO: 11. The plant, the plant cell, the plant material or the seed of the plant that expresses the exogenous XPO1A protein has basal thermotolerance under long-term heat stress and sudden heat shock condition.

In accordance with one embodiment of the present disclosure, the promoter is a constitutive promoter or an inducible promoter.

In accordance with one or more embodiments of the present disclosure, wherein the isolated nucleic acid sequence comprises a polynucleotide sequence of SEQ ID NO: 1, a polynucleotide sequence of SEQ ID NO: 2 or a polynucleotide sequence of SEQ ID NO: 3.

In another aspect of the present disclosure, a method of producing a transformed plant cell is disclosed. The method includes following steps. A polynucleotide that encodes an exogenous XPO1A protein of SEQ ID NO: 11 is introduced into a plant cell. The exogenous XPO1A protein is expressed in the plant cell. The plant cell that expresses the exogenous XPO1A protein has basal thermotolerance.

In another aspect of the present disclosure, a method of producing a so transformed plant is provided. The method includes following steps. A polynucleotide that encodes an exogenous protein and an exogenous XPO1A protein of SEQ ID NO: 11 is introduced into a plant cell. The exogenous protein and the XPO1A protein are expressed in the plant cell. A whole plant from the plant cell is regenerated at a survivable temperature. The transgenic plants are subjected to a sustained high temperature or a sudden heat shock treatment, wherein a sustained high temperature or a heat shock temperature is equal to or higher than a lethal temperature of a non-transgenic plant. After the treatment, the transgenic plant survived after sustained high temperature or sudden heat shock treatment is selected. The survived transgenic plant expresses the exogenous protein and the exogenous XPO1A protein under sustained high temperature or sudden heat shock condition.

In accordance with one embodiment of the present disclosure, the polynucleotide comprises a polynucleotide sequence of SEQ ID NO: 1.

In accordance with one or more embodiments of the present disclosure, the polynucleotide sequence of SEQ ID NO: 1 is operably linked to a constitutive promoter or an inducible promoter.

In accordance with one or more embodiments of the present disclosure, the polynucleotide comprises a polynucleotide sequence of SEQ ID NO: 2 or a polynucleotide sequence of SEQ ID NO: 3.

In accordance with one or more embodiments of the present disclosure, the plant cell belongs to Brassicaceae family or tomato.

In accordance with one or more embodiments of the present disclosure, the plant cell belongs to *Arabidopsis* genus or tomato.

In accordance with one or more embodiments of the present disclosure, recombinant vector is introduced into the plant cell by using a plasmid or a viral vehicle.

In accordance with one or more embodiments of the present disclosure, the plasmid is a Ti-plasmid.

It is to be understood that both the foregoing general description and the following detailed description are by examples, and are intended to provide further explanation of the disclosure as claimed.

BRIEF DESCRIPTION OF THE DRAWINGS

The disclosure will be illustrated with respect to the accompanying figures and examples, which serve to illustrate this disclosure but are not binding thereon, wherein.

DETAILED DESCRIPTION

Figure 1:
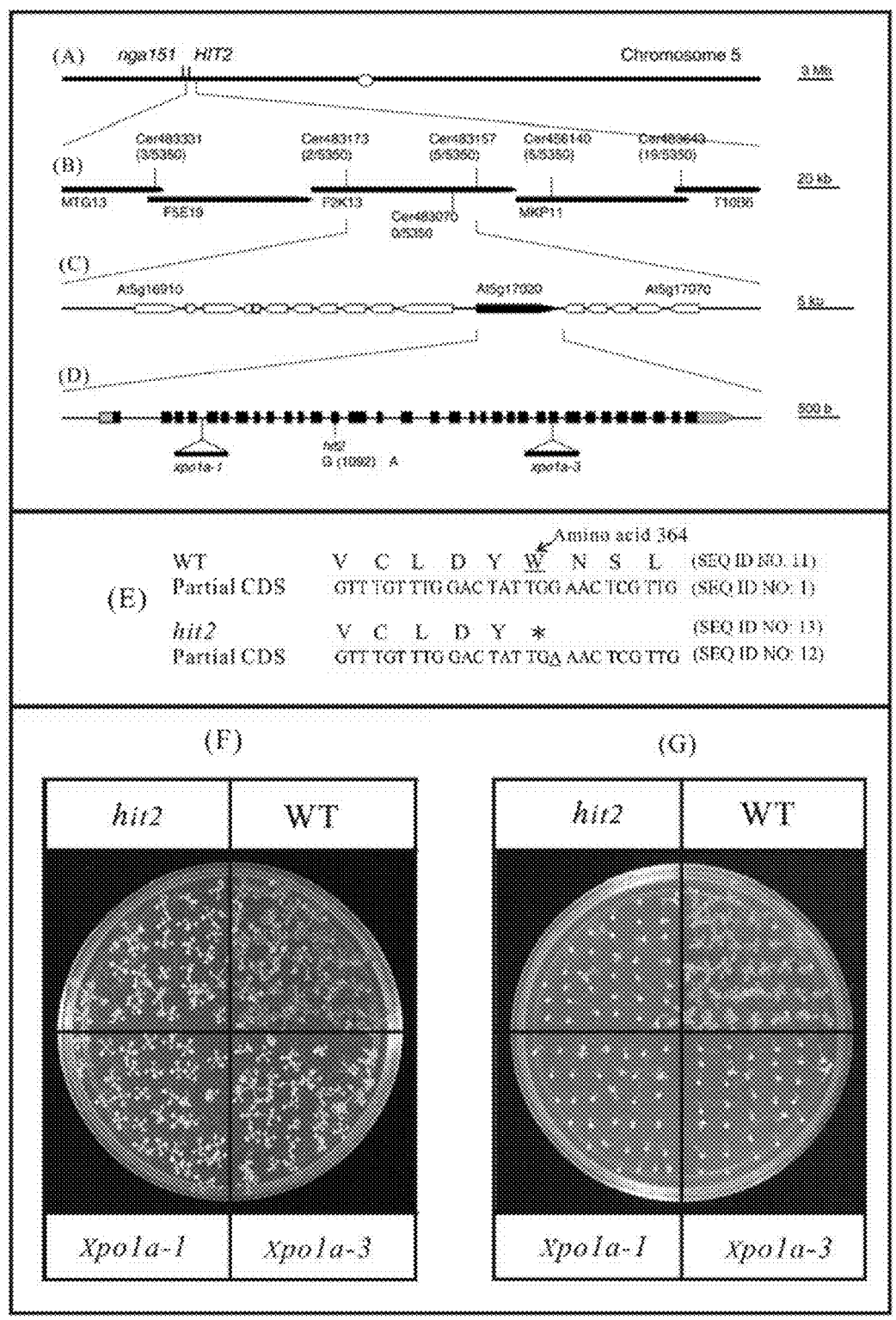
FIGS. 1(A) to 1(G) illustrate the recombination mapping of the heat-intolerant 2 (hit2) locus.

In the following detailed description, for purposes of explanation, two parts are set forth in order to provide a thorough understanding of the disclosed embodiments and their theoretical basis.

Part 1 provides numerous physiological experiments of an Arabidopsis heat-intolerant 2 (hit2) mutant to build the theoretical basis of relationship of XPO1A protein and the basal thermotolerance of plant.

In accordance with the evidences of Part 1, Part 2 further discloses numerous examples for confirming effects of a transgenic plant with an exogenous polynucleotide encoding a XPO1A protein. Part 2 also provides some specific details that are essential for inducing the phenotype of thermotolerance of the transgenic plant. It will be apparent, however, that one or more embodiments may be practiced without these specific details.

The "basal thermotolerance" of plants herein is referred to survival without pretreatment. The plants with basal thermotolerance can survive under long-term heat stress (37° C. for 3-4 days) or sudden heat shock (44° C. for 30 min).

The XPO1A protein of the present disclosure is introduced into a plant cell for enhancing the "basal thermotolerance" but not the "acquired thermotolerance" because "acquired thermotolerance" is referred to the thermotolerance induced after moderate and non-lethal heat stress. For example, incubation at 44° C. for 1 h is lethal for the plants. But after 1 h of pretreatment at 37° C., the plants are able to withstand heat shock at 44° C. for 1 h.

Part 1: Functional Analysis of XPO1A (1) Obtaining of the Arabidopsis Heat-Intolerant 2 (hit2) Mutant The genome of Arabidopsis thaliana, with five chromosomes containing about 114.5 million base pairs, had been completely sequenced in 2000 by Arabidopsis Genome Initiative. Since the relative shorter life cycle, smaller body and larger amount of offspring than those of most of plants, Arabidopsis is broadly used in genetics and molecular biology approaches. Moreover, numerous Arabidopsis mutants and genomic data are accumulated from the routine work of transferring DNA to Arabidopsis by utilizing Agrobacterium tumefaciens with Ti-plasmid conjugal transfer system. The information of ecotypes of Arabidopsis, such as Columbia (Col), Landsberg erecta (Ler), Wassilewsdiaja (Ws), etc., or the polymorphism of the ecotypes can be obtained from library and internet resources.

For purpose of improving the thermotolerance of a plant, a forward genetics approach was used to find out a gene related essentially to the thermotolerance of plant. A heat intolerant mutant, hit2, exhibited the phenotype of heat intolerance was isolated from Arabidopsis thaliana ecotype Columbia-0 (Col-0). A gene encoding XPO1A (XPO1A, At5g17020) was mutated and therefore exhibited the heat intolerance phenotype. The codon for tryptophan 364 (TGG) of the XPO1A gene changed to a premature TGA stop codon is recognized by a map-based cloning approach. That is, the G to A mutation of the XPO1A gene of Arabidopsis creates the heat intolerance phenotype of the mutant.

Arabidopsis contains two copies of the XPO1 genes, XPO1A (At5g17020) and XPO1B (At3g03110). In general, it was believed that XPO1A and XPO1B might have the same function and could produce complementary or synergistic effects.

In view of the gene conservation, the gene product of XPO1A is a nuclear transport receptor. The nuclear transport receptor may be employed to transfer substrates from nuclear to cytoplasm in a plant cell. However, the real mechanism of the nuclear transport receptor in the plant cell has not been fully understood yet. Also, there was no finding about the relationships between XPO1A protein and thermotolerance of plants.

According to the studies of nuclear transport receptors, a nuclear transport receptor transports a target protein by recognizing a specific amino acid sequence of the target protein. A nuclear transport receptor can recognize and transport one or more proteins with a specific amino acid sequence. Similarly, a protein having the specific amino acid sequence can be recognized and transported by one or more nuclear transport receptors. For the foregoing reasons, if a gene mutation occurred in a nuclear transport receptor of an organism, the physiological function of the nuclear transport receptor could be accomplished by another nuclear transport receptor. Hence, the phenotype of the organism may not be changed. On the other hand, a mutation occurred in a single nuclear transport receptor is also likely to affect transportation of one or more proteins and therefore changes the phenotypes of the mutant.

The Arabidopsis heat-intolerant 2 (hit2) mutant was analyzed by following experiments to identify the function of XPO1A, including genetic characteristics of the hit2 mutant, physiological experiments of thermotolerance of the hit2 mutant, and expression of XPO1A gene in plant tissues.

(2) Characterizing the Single Recessive Nuclear Mutation of the hit2 Mutant

The genetic characteristics of the hit2 mutant can be analyzed by interbreeding (crossing) the mutant (hit2) with a wild-type plant to identify whether the mutant is recessive or dominant. Furthermore, map-based cloning is used to localize the locus of the mutation.

To identify whether hit2 is a recessive or a dominant and a single or a multiple mutation, wild-type *Arabidopsis* plants in the Columbia gl-1 background (Col-5) is employed as female gametophytes to interbreed with the mutant (hit2, in Col-0 background) that is employed as male gametophytes. Crosses between mutant and wild-type are accomplished by transferring pollen from the mutant to the stigma of emasculated wild-type flowers. The leaf trichomes will present in the $F_1$ plants if the crossing succeeds. $F_1$ plants are self-pollinated to produce the $F_2$ generation.

Table 1 is a summary of genetic analysis results of the *Arabidopsis* heat-intolerant 2 (hit2) mutant and exportin1b (xpo1b-1) mutants. 143 wild-type Col-0, 140 hit2, 57 $F_1$ from a cross between hit2 and wild type, 440 $F_2$ from self-pollinated $F_1$, and 45 xpo1b-1 plants were analyzed. These plants were tested for their heat sensitivity by planting seeds on MS agar plates at 22° C. for 10 days followed by treatment at 37° C. for 4 days. This treatment was shown to be lethal for the hit2 mutant but not for wild-type (Col-0) seedlings. As shown in table 1, all of the 143 wild type seedlings survived and all of the 140 seedlings of heat-intolerant 2 (hit2) mutant were bleached and dead (Tolerance=0). The 57 heterozygous seedlings (hit2×Col-5 $F_1$) also survived after the treatment. In 440 $F_2$ seedlings (hit2×Col-5 $F_2$), 327 seedlings of them survived and 133 seedlings of them exhibited heat sensitivity and were bleached completely after the heat treatment. Mutation at xpo1b did not affect the plant heat sensitivity as all of the 45 xpo1b-1 seedlings tested survived after the heat treatment. Furthermore, analysis of the self-pollinated $F_2$ plants showed a 2.89:1 segregation ratio of wild-type to hit2 plants. Hence, the heat intolerance phenotype was caused by a single recessive nuclear mutation.

that occurs during meiosis. Crossing-over of the chromosomes during meiosis leads to genetic recombination, and the recombination frequency between different genes on a chromosome can be used to estimate their order and distances apart. In general, the closer two genes are on a chromosome, the more co-segregation is, that is, the less likely it is that crossing-over will occur between them. Therefore, the map-based cloning is to identify molecular markers on a known gene, and calculate the recombination frequency to estimate locus of the mutant.

Ecotype-specific genetic markers were used for mapping of the *Arabidopsis* heat-intolerant 2 (hit2) locus. Initially, identify two sets of genetic markers on each chromosome. For rough mapping, the marker near the mutated locus (hit2) was recognized. New markers located in the vicinity of the previous marker were then found to locate the hit2 mutation.

Useful methods to analyze the different ecotypes in species include, but are not limited to simple sequence length polymorphism (SSLP) and cleaved amplified polymorphic sequence (CAPS). SSLPs are used as genetic markers that detect differences in the length of a genomic region. Typically the differences are due to small insertions or deletions (In-Dels) such as those caused by differences in the number of simple sequence repeats. For SSLP, primers complementary to a given genomic region are used to amplify the region from genomic DNA by polymerase chain reaction (PCR) and the resulting PCR products are separated on an agarose gel. Variances in the length of SSLPs are used to understand genetic variance between two individuals in a certain species (Ponce M R 1999, Lukowitz W et al. 2000, Peters et al. 2003). SSLP and CAPS are by far the most commonly used genetic markers. Since these markers are co-dominant, both alleles can be identified to provide sufficient information. Furthermore, it is convenient and low-cost to perform PCR-based markers analysis, and the resulting products are analyzed directly by agarose gel electrophoresis (Lukowitz W. et al. 2000). Publicly available genetic markers which are specific to *Arabidopsis* ecotypes can be searched on TAIR. Markers that are based on insertions/deletions (INDELs) and single nucle-

TABLE 1

Genetic analysis of the Arabidopsis heat-intolerant 2 (hit2) and exportin 1b-1 (xpo 1b-1) mutants

| Strains or crosses (♂ × ♀) | Generation | Total | Tolerant[a] | Sensitive[a] | $\chi^{2b}$ |
|---|---|---|---|---|---|
| Wild-type (Col-0) | | 143 | 143 | 0 | |
| hit2/hit2 | | 140 | 0 | 140 | |
| Wild-type × hit2/hit2 | $F_1$ | 57 | 57 | 0 | |
| | $F_2$ | 440 | 327 | 113 (34.6%) | 0.109[b] |
| xpo 1b-1/xpo 1b-1 | | 45 | 45 | 0 | |

[a]Tolerance or sensitivity was determined in the survivability assay as described in the Materials and Methods section.
[b]The calculated v2 value was based on the expected ratio of 3:1 for tolerant to sensitive individuals, assuming that hit2 was a single recessive mutation (P > 0.05).

The present disclosure demonstrates that the XPO1A protein plays an important role of assisting plant to resist long-term heat stress. Moreover, the heat intolerance phenotype can be created by XPO1A gene single mutation.

(3) Characterizing the Single Recessive Nuclear Mutation of the hit2 Mutant

Genetic analysis revealed that heat-intolerant 2 (hit2) mutant is a single recessive mutation. To determine the genetic determinant that underlines the mutant (hit2) thermosensitive phenotype, map-based cloning, also called positional cloning, was employed to identify the hit2 locus. The method of map-based cloning relies on the process of chromosomal crossing-over between the paired chromosomes otide polymorphisms (SNPs) can also be identified from Cereon *Arabidopsis* Polymorphism Collection by comparing the genomes of *Arabidopsis* ecotype Columbia and Lansberg. Primers are then designed for SSLP and CAPS.

Initially, rough mapping located the mutation on the upper arm of chromosome 5 near the molecular marker so262 with 17.8% of recombination frequency. Further mapping localized the hit2 locus to a c. 1.3-Mb region that was delimited by the genetic markers nga51 and Cer456932 (Wang, 2006). The genetic markers Cer483173 and Cer483157 were selected for fine mapping that localized the hit2 locus further to a c. 60 kb region. Genomic DNA from hit2 plants was sequenced in this region and compared with that from wild-type plants. The mutated locus was mapped to the EXPORTIN1A (XPO1A) gene, which encodes the nuclear export receptor XPO1A. A person having ordinary skill in the art can accomplish the experiments described above using conventional techniques. On the other hand, the person having ordinary skill in the art can readily appreciate how to make and use the same by referring the following published paper "Isolation and characterization of the *Arabidopsis* heat-intolerant 2 (hit2) mutant reveal the essential role of the nuclear export receptor EXPORTIN1A (XPO1A) in plant heat tolerance" (New Phytologist (2010) 186:833-842, www.newphytologist.com), and the details of the paper are incorporated in the present disclose.

FIGS. 1(A) to 1(G) illustrate the recombination mapping of the HEAT-INTOLERANT 2 (HIT2) locus. FIG. 1(A) indicates *Arabidopsis* chromosome 5 with simple sequence length polymorphism (SSLP) marker nga151, which is adjacent to the HIT2 locus. FIG. 1(B) shows expansion of the region that encompasses the HIT2 locus. Five overlapping bacterial artificial chromosomes within the region are shown. The relative positions of the molecular markers (vertical lines) are indicated. The number of recombinants versus the total number of chromosomes tested for a given marker is shown in parentheses. FIG. 1(C) is the chromosomal region between markers CER483173 and CER483157, which was sequenced and compared with that of the wild type. The gene shown in black represents At5g17020, in which a single base substitution was found in the hit2 mutant plants. Exon-intron structure of the HIT2 gene is shown as FIG. 1(D). The hit2 mutation is a G-to-A mutation within the 13th exon of At5g17020. This gene encodes the nuclear export receptor XPO1A. Additional T-DNA insertion alleles of At5g17020, exportin1a-1 (xpo1a-1) and exportin1a-3 (xpo1a-3), are also indicated. FIG. 1(E) indicates a nucleotide change found in hit2 (SEQ ID NO: 12) corresponded to a nonsense mutation that truncated the HIT2 protein (SEQ ID NO: 13) at amino acid 364.

FIG. 1(F) shows phenotypes of 10-day-old wild-type, hit2, xpo1a-1, and xpo1a-3 plants after incubation at 37° C. for 4 days. Phenotypes of wild-type, hit2, xpo1a-1, and xpo1a-3 *Arabidopsis* seedlings after heat shock at 44° C. for 20 min are shown as FIG. 1(G). In the heat survivability assay or after heat shock treatment, wild-type seedlings could survive, but xpo1a-1 and xpo1a-3 homozygous seedlings exhibited the same thermosensitive phenotype as that of hit2.

(4) Physiological Analysis of Heat-Intolerant 2 (hit2) Mutant

To evaluate the role of XPO1A gene in defense against heat stress, the physiological experiments were performed, including the effects of heat shock, the sensitivity to heat or oxidative stress and the influence of heat-induced oxidative stress and light conditions. The hit2 mutant and wild-type seedlings were compared to identify the functions of XPO1A.

1. The Effects of Heat Shock on the Phenotypes of Wild-Type and hit2 Seedlings

The hit2 mutant was isolated on the basis of its impaired ability to withstand sustained high temperature. Hence, the response of hit2 to heat shock was investigated to understand the relationships between the mechanisms by which plants cope with heat shock and prolonged heat stress.

Figure 2:
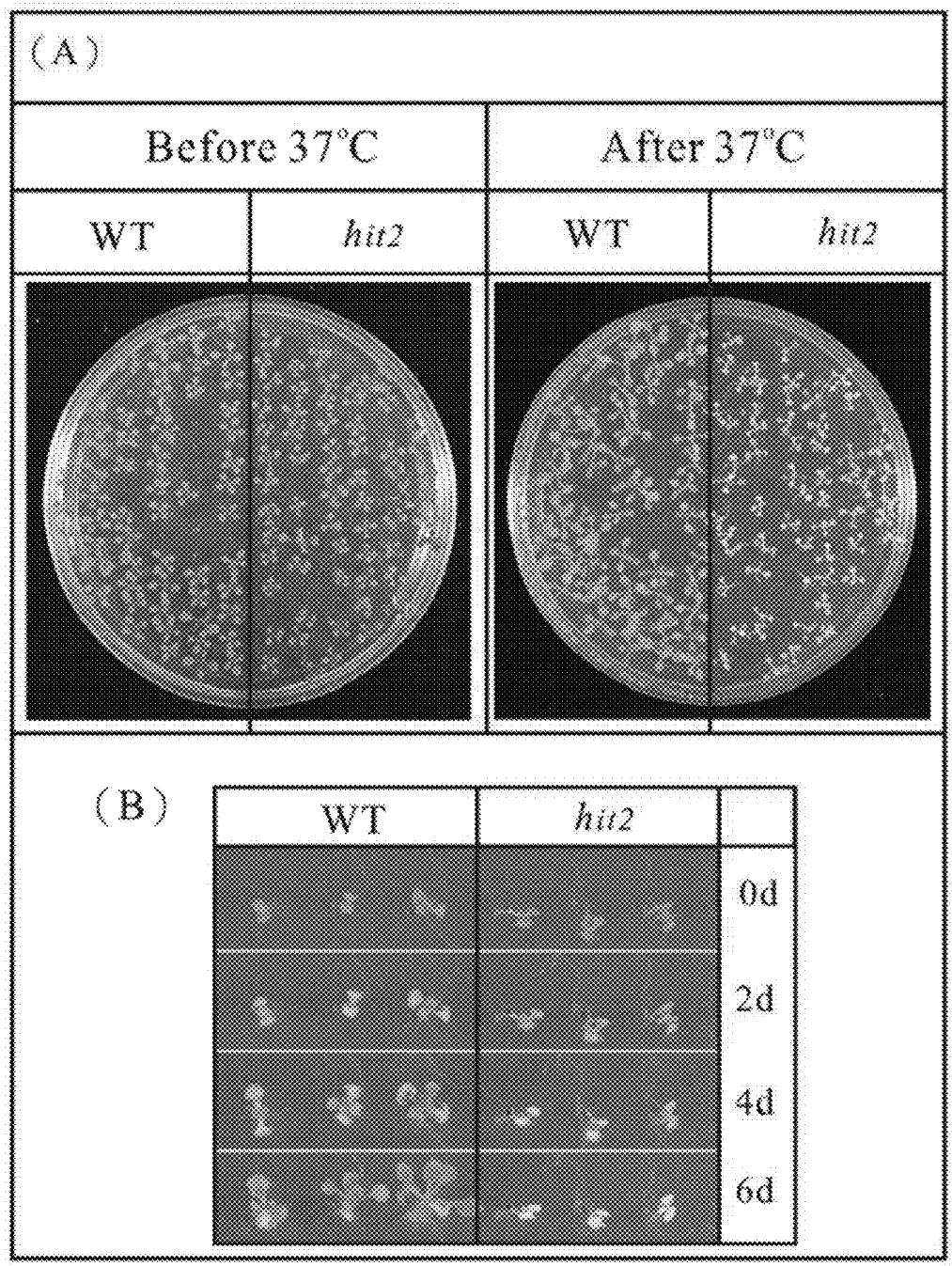
FIGS. 2(A) to 2(B) are photographs showing the sensitivity of Arabidopsis heat-intolerant 2 (hit2) mutant to sustained high temperature and sudden heat shock.
Figure 3:
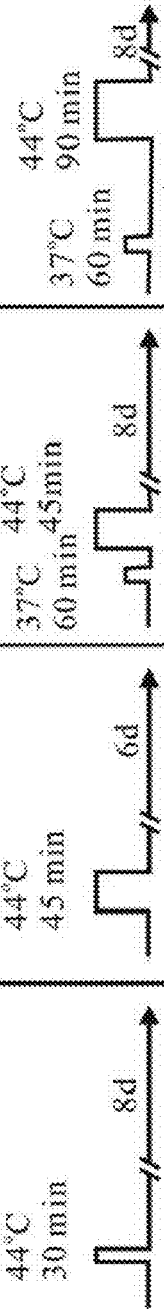
FIGS. 3(A) to 3(D) are photographs showing the viability of wild-type and hit2 seedlings after different heat stress treatments.

FIGS. 2(A) to 2(B) are photographs showing the sensitivity of *Arabidopsis* heat-intolerant 2 (hit2) mutant to sustained high temperature and sudden heat shock. FIG. 2(A) is photographs taken before and after heat exposure at 37° C. for 4 days. Progression of phenotypes of wild-type and hit2 seedlings after heat shock treatment is shown as FIG. 2(B). Seven-day-old plants grown on medium, with opened cotyledons and an emerging first pair of leaves, were subjected to heat shock at 44° C. for 20 min. After treatment, plants were returned to room temperature for recovery and photography.

There is no difference between wild-type and hit2 plants before 37° C. treatment. However, incubation at 37° C. for 4 days was lethal for hit2 but not wild-type plants (FIG. 2(A)). FIG. 2(B) shows the development of the seedlings after they were exposed to heat shock for 20 min. No difference in appearance between the mutant and wild-type seedlings was observed immediately after treatment. However, after 6 days at 23° C., the leaves of wild-type seedlings remained green in color and exhibited noticeable growth and expansion, whereas the leaves of the hit2 seedlings were bleached completely and showed no sign of growth.

2. The Influence of Sub-Lethal Pre-Acclimation on the Survival Rates of Wild-Type and hit2 Seedlings to Otherwise Lethal Heat Shock Treatment FIGS. 3(A) to 3(D) are photographs showing the viability of wild-type and hit2 seedlings after different heat stress treatments. Seven-day-old seedlings grown on medium were subjected to the different heating regimens indicated above each photograph. Survival rates were calculated from the number of seedlings that showed continuous growth of green leaves after 6 days.

Treatment (A) was that plants were exposed to 44° C. for 30 min and then incubated at 23° C. Plants were exposed to 44° C. for 45 min and incubated at 23° C. in treatment (B). Treatment (C) was that plants were pre-acclimated at 37° C. for 60 min and incubated at 23° C. for 60 min, followed by treated at 44° C. for 45 min. After pre-acclimation at 37° C. for 60 min, the plants were incubated at 23° C. for 2 days and exposed to 44° C. for 90 min in treatment (D). Apart from heat treatment, plants were incubated at 23° C. Plates were photographed at 6-8 days after the final heat treatment.

The survival rate of wild-type seedlings in treatment (A) was 95%, whereas that of hit2 seedlings was 0%. Neither wild-type nor hit2 seedlings in treatment (B) could survive after 6 days. However, after 1 h of pre-acclimation at 37, hit2 plants were able to survive heat shock that was otherwise lethal, as were wild-type (WT) plants (C,D). These results implied that the hit2 mutants were defective in basal but not acquired thermotolerance.

3. The Effects of Oxidative Stress on the Phenotypes of Wild-Type and hit2 Seedlings FIGS. 4(A) to 4(D) are diagrams illustrating the seed germination and seedling development of wild-type and hit2 on medium that contained various concentrations of methyl viologen (MV). Seeds were sown on agar plates that contained various concentrations of methyl viologen (MV) and allowed to germinate at 23° C. with continuous illumination. Methyl viologen is a common inducer of oxidative stress. FIGS. 4(A) to 4(C) indicate the percentage of seeds that germinated or matured. The open circles represent *Arabidopsis* heat-intolerant 2 (hit2) seedlings, and the closed circles are wild-type seedlings. Data for plots were obtained from a sample size of c. 60 seeds on each plate, and at least three replicated plates were used for each treatment. Error bars represent SD for all experiments. FIG. 4(D) shows the phenotypes of representative wild-type and mutant seedlings grown at 0.5 µg MV for 14 days. Seedlings from the same plate were removed and reorganized for the photograph.

FIG. 4(A) is the percentage of seeds that germinated. It was determined by counting the seeds with visible protruding radicals after 10 days. The percentage of seedlings that matured in FIG. 4(B) was calculated from the number of seeds that showed green opened cotyledons after 14 days.

FIG. 4(C) is the progression of seedling maturation of wild-type and hit2 seeds sown on agar supplemented with 0.5 µM MV.

As shown in FIG. 4(A), wild-type and hit2 mutant seeds exhibited similar germination rates at various concentrations of MV. Seed germination of the hit2 mutant was relatively unaffected by MV inhibition. However, the development of hit2 seedlings was more sensitive to inhibition by treatment with MV than that of wild-type seedlings (FIG. 4(B)). Furthermore, although some of the hit2 seeds were able to reach the seedling stage, their cotyledons soon became pale and their growth ceased (FIGS. 4(C) and 4(D)). The decline in maturation rate of hit2 seedlings after day 7 might have been caused by fading of the green color of the cotyledons of hit2 seedlings that had developed.

Figure 4:
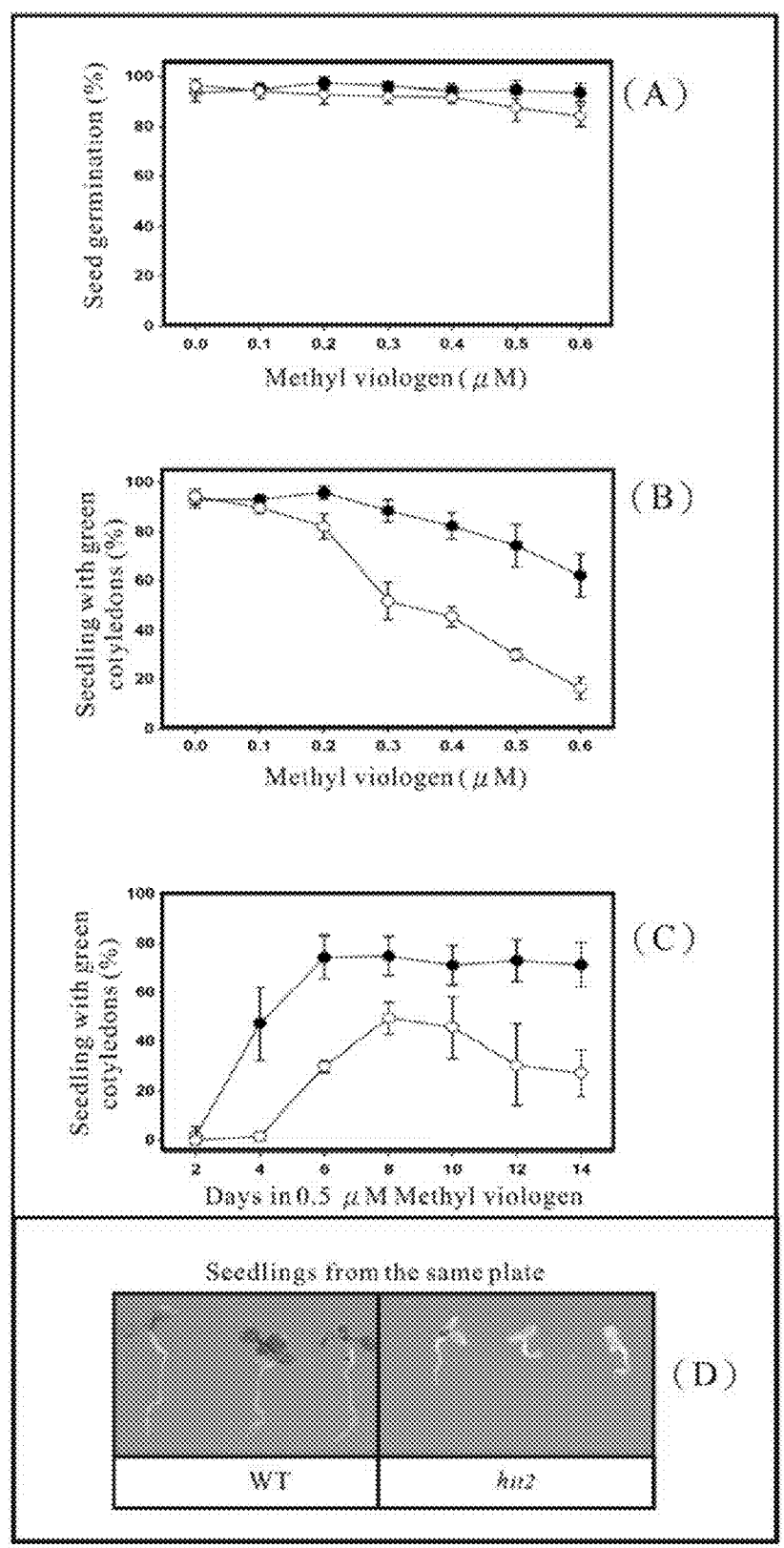
FIGS. 4(A) to 4(D) are diagrams illustrating the seed germination and seedling development of wild-type and hit2 on medium that contained various concentrations of methyl viologen (MV)

4. The Effects of Heat-Induced Oxidative Stress and Light Conditions on Survival of Wild-Type and hit2 Seedlings Heat-induced oxidative damage is known to be exacerbated by light, and the light conditions to which plants are exposed have been shown to influence plant survival after heat stress (Larkindale and Knight, 2002; Larkindale et al., 2005). As shown in FIG. 4, hit2 is sensitive to MV-induced photo-oxidative stress, and therefore it is likely that light conditions will affect the sensitivity of hit2 to heat. To confirm the relationships between light conditions and the heat sensitivity of hit2, hit2 seedlings were subjected to the heat survivability assay as before, but the plants were protected from exposure to light.

Figure 5:
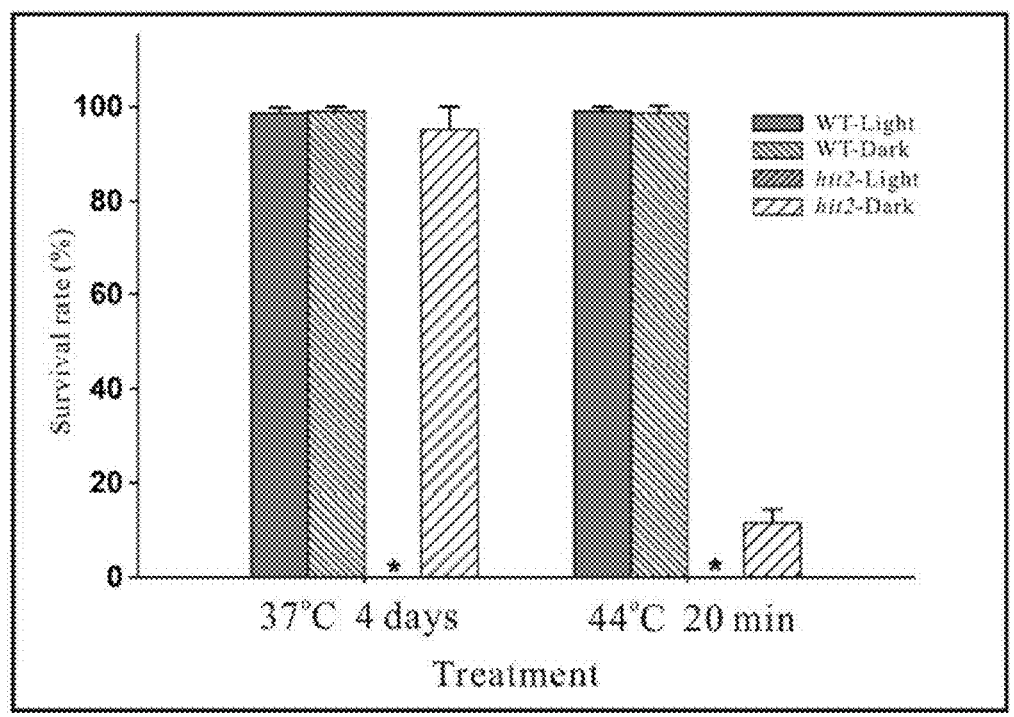
FIG. 5 is a bar diagram illustrating the survival rate of Arabidopsis wild-type and hit2 seedlings after heat treatment in the light or dark.

FIG. 5 is a bar diagram illustrating the survival rate of *Arabidopsis* wild-type and hit2 seedlings after heat treatment in the light or dark. Ten-day-old plants grown on medium were heated to 37° C. in the light or dark for 4 days. Seven-day-old seedlings were heated to 44° C. for 20 min and allowed to recover at 23° C. in the light or dark for 6 days. The numbers of plants that were alive before and after treatment were counted to determine the survival rate. Data shown are the averages of six replicates; error bars represent SD. * represents zero survival rates.

FIG. 5 shows that the viability of hit2 seedlings after long-term heat stress (37° C. for 4 days) was increased markedly, from zero survival in the light to near total survival in the dark. In the case of heat shock stress, hit2 seedlings were treated at 44° C. for 20 min as before, but were allowed to recover in the dark. Again, the survival of hit2 seedlings was increased, but to a much lesser extent; only 10% of the hit2 seedlings were able to recover from the stress treatment. This phenomenon might have been caused by other forms of damage, which were more severe than heat-induced oxidative injury and which occurred rapidly in heat-shocked hit2 seedlings, and masked the influence of light during later recovery. Collectively, these results indicate that the hit2 phenotype is attributable, at least in part, to the lack of a sufficient response to oxidative injury, which strongly affects hit2 viability under sustained high temperature condition, but is less significant for protection against heat shock. Heat stress will cause overproduction of reactive oxygen species, and light make heat-induced oxidative damage worse. Hence, the results shown as FIG. 5 indicated that XPO1A might have the ability to protect the plants from heat-induced oxidative damage.

5. The Effect of Heat Stress on XPO1A Gene Expression

To evaluate the expression of XPO1A gene, total RNA was extracted from different tissues of wild-type seedlings. The 3' region of the XPO1A cDNA was amplified by semiquantitative RT-PCR using primers SEQ ID NO 4 and SEQ ID NO 5 and analyzed by agarose gel electrophoresis.

Figure 6:
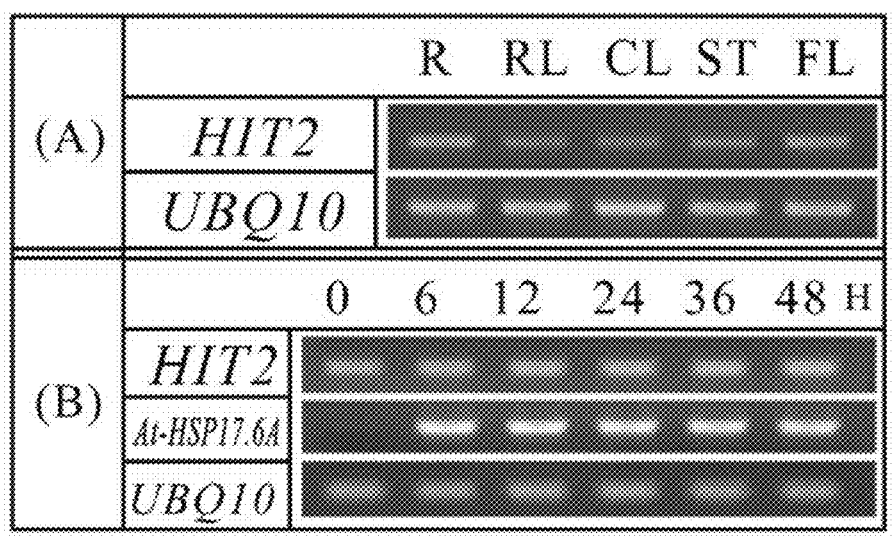
FIGS. 6(A) to 6(B) are agarose gel electrophoresis diagrams illustrating the expression of XPO1A in wild-type plants.

FIG. 6(A) is an agarose gel electrophoresis diagram illustrating the expression of XPO1A in hit2 plants. Reverse transcription-polymerase chain reaction (RT-PCR) was performed on first-strand cDNA generated from different *Arabidopsis* plant tissues grown at 23° C. (FIG. 6(A)). Tissue designations were as follows: R, root; RL, rosette leaf; CL, cauline leaf; ST, stem; FL, flower. Poly-ubiquitin (UBQ10) RNA served as an internal control for RT-PCR. The XPO1A transcript was detected in the root, rosette leaves, cauline leaves, stem, and flowers, which suggested that XPO1A was expressed ubiquitously in sporophytic tissues.

FIG. 6(B) shows the effect of heat stress on XPO1A expression. Total RNA for RT-PCR analysis were extracted from 10-day-old seedlings that had been incubated at 37° C. for 0, 6, 12, 24, 36, or 48 h, respectively. Heat shock protein 17.6A (At-HSP17.6A) RNA served as a positive control. Although expression of the heat-responsive small HSP gene AtHSP17.6A was induced within 6 h, XPO1A was expressed at a relatively constant level throughout the treatment.

XPO1A has a different function from that of XPO1B under heat stress conditions. The results demonstrated that *Arabidopsis* XPO1A is dispensable for normal plant growth and development but is essential for thermotolerance. The importance of XPO1A in plants against heat stress provides new insights into its role in heat tolerance.

Part 2: Applications and Embodiments

One embodiment of this disclosure is to transfect an exogenous polynucleotide encoding a XPO1A protein into plants. Therefore, the transgenic plants can express exogenous XPO1A and be able to survive under heat stress.

The gene encoding XPO1A is XPO1A gene or a sequence which shares homology and analogy with XPO1A gene. The sequence described above can be obtained by isolation from appropriate seedlings or be synthesized artificially. Plants having the gene encoding XPO1A include, but are not limited to Brassicaceae plants, such as *Arabidopsis*. A person having ordinary skill in the art can obtain the sequence encoding XPO1A by conventional procedures.

The gene described above, which is XPO1A gene or a sequence sharing homology and analogy with XPO1A gene, includes the sequence of SEQ ID NO 1, its complementary sequences, and conservative analogs. For example, a homologous sequence having degenerative codon substitutions. Degenerative codon is that more than one triplet sequence of codons can specify the insertion of the same amino acid into a polypeptide chain.

In the embodiments of this disclosure, XPO1A gene or the sequence sharing homology and analogy with XPO1A gene were used to construct the plasmid that encoded XPO1A. The plasmid was then transfected into plants to generate transgenic plants that could withstand high temperature conditions. The plant tissues or cells that are appropriate for the disclosure include, but are not limited to roots, stems or leaves of Brassicaceae or tomato.

Suitable transfection methods for the disclosure include, but are not limited to calcium phosphate, gene gun, microinjection, electroporation, liposome, etc. The gene that encodes XPO1A was transfected into plant tissues or cells.

The vectors that can be used in the disclosure include, but are not limited to the plasmid that encodes XPO1A or viral vectors that infects plants to transfect plant tissues or cells.

For example, plasmids can be transfected into plant cells by bacteria-mediated transformation. The bacteria may include but are not limited to *Agrobacterium tumefaciens*. For gene transfer, Ti-plasmids comprising a polynucleotide sequence which encodes XPO1A are transfected into plant cells, or viral vectors are used to infect cells for introducing XPO1A gene. In one embodiment, the vectors comprise a polynucleotide sequence of SEQ ID NO 1.

The polynucleotide encoding XPO1A protein comprises a promoter that is linked to the upstream region of XPO1A gene or a polynucleotide sequence of SEQ ID NO: 1. The promoter is a constitutive promoter or an inducible promoter, such as 35S promoter or AlcA promoter (enthanol-inducible system). In one embodiment, the polynucleotide encoding a XPO1A protein comprises a constitutive promoter and a polynucleotide sequence of SEQ ID NO: 1. The polynucleotide comprising polynucleotide sequence of SEQ ID NO: 1 is a polynucleotide sequence of SEQ ID NO: 2. In other embodiment, the polynucleotide encoding a XPO1A protein comprises an inducible promoter and a polynucleotide sequence of SEQ ID NO: 1. The polynucleotide comprising polynucleotide sequence of SEQ ID NO: 1 is a polynucleotide sequence of SEQ ID NO: 3.

Unless otherwise indicated, promoter regions described herein comprise sequences recognized by RNA polymerase, regulatory sequences, constitutive promoter or inducible promoter sequences and transcription initiation site.

In addition, for each plant, the codon or promoter preferred by host cells are used to promote the expression of exogenous XPO1A protein.

According to another embodiment of this disclosure, the polynucleotide encoding XPO1A is utilized as a selection marker of transgenic plants. The recombinant plasmid comprising target gene and the selection marker was transfected into plant. By long-term high temperature stress or heat shock treatment, the transgenic plant with basal thermotolerance phenotype can be isolated.

The following embodiments are provided to describe methods of the present disclosure and the effects of XPO1A gene on the ability of plants to withstand heat stress.

EMBODIMENTS

1. Construction of pCAMBIA1300-XPO1A

Figure 7:
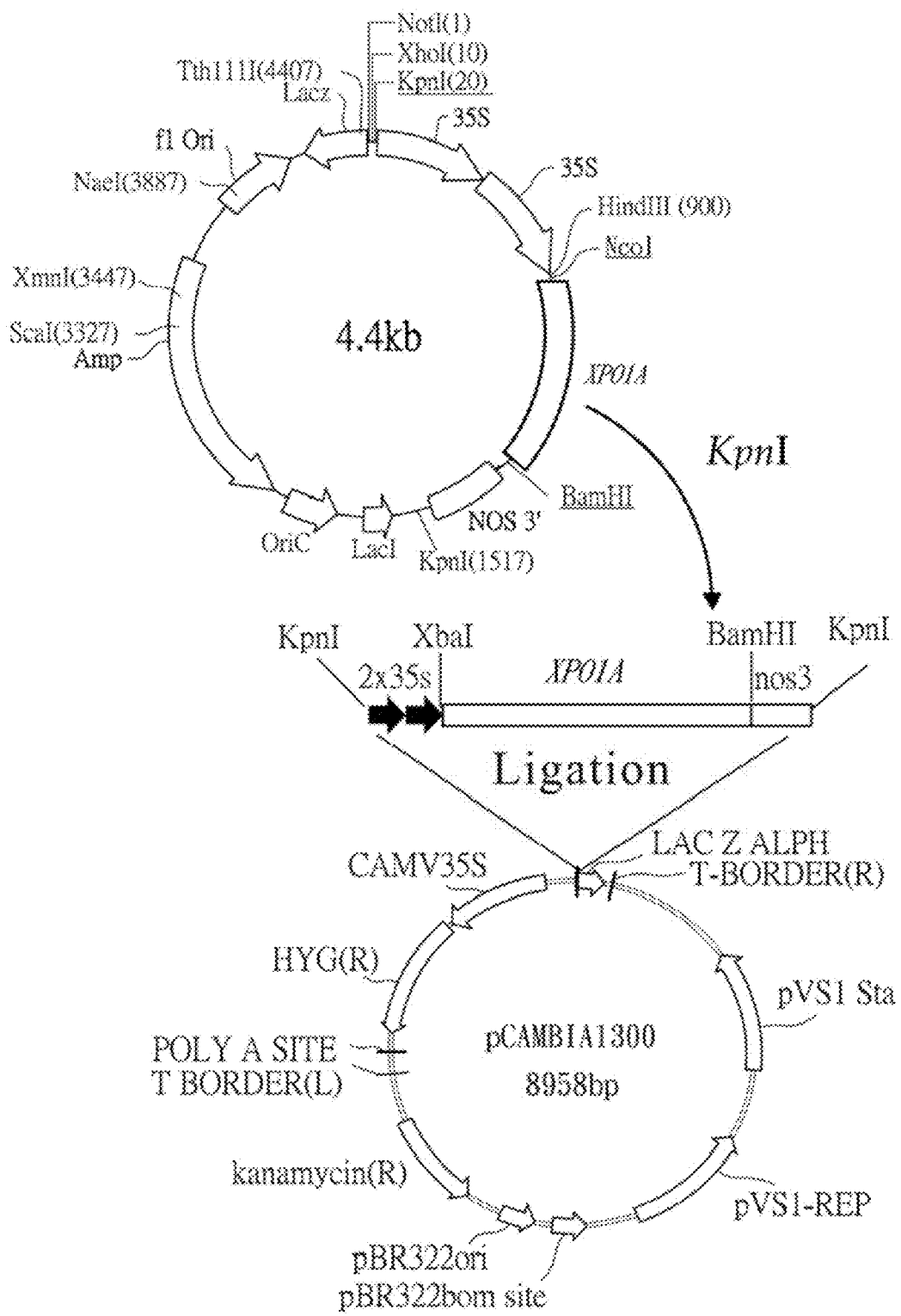
FIG. 7 illustrates a schematic diagram of the plasmid of pCAMBIA1300-XPO1A.

FIG. 7 illustrates a schematic diagram of the plasmid of pCAMBIA1300-XPO1A. In the embodiment, the chromosome of *Arabidopsis thaliana* was served as the template and primers SEQ ID NO 6 and SEQ ID NO 7 were used to amplify the XPO1A gene which is shown as SEQ ID NO 2 by PCR.

The amplified fragments and the vector pLOLA were digested by restriction enzymes NcoI and BamHI. The sequences of XPO1A gene were cloned into the vector via restriction sites for NcoI and BamHI using $T_4$ DNA ligase to obtain pLOLA-35S-XPO1A-nos.

Digestion of pLOLA-35S-XPO1A-nos by KpnI generated the sequences which contain promoter (SEQ ID NO 8), XPO1A gene and terminator (SEQ ID NO 9). The sequences which encoded XPO1A protein were ligated into the vector pCAMBIA1300 digested by KpnI using $T_4$ DNA ligase to obtain pCAMBIA1300-XPO1A (SEQ ID NO 10).

To construct the plasmids, mRNA was extracted from plant tissues by commercial kit (Genemark Plant Total RNA Miniprep Purification Kit) or traditional extraction methods. The purified RNA was stored at −70° C. Reversed transcription was performed using SuperScript™ II Reverse Transcriptase (Invitrogen). For cDNA synthesis, 5 µl (1 ng-5 µg) RNA solution was first incubated with 1 µl of Oligo dT (500 µg/µl), 1 µl of dNTP (10 mM) and 5 µl of DEPC-treated water. After incubation for 5 min at 65° C. to denature RNA secondary structure, the mixture was then quickly chill on ice to let the primer anneal the RNA. Four µl of 5× first-stand buffer, 1 µl of RNase inhibitor (40 U/µl) and 2 µl of DTT (0.1M) was then added. The mixture was incubated for 2 min at 42° C. Add 1 µl (200 U) of SuperscriptII Reverse Transcriptase and incubate at 42° C. for 50 min. The reaction was then terminated at 70° C. for 15 min and stored at 4° C. For removing unreacted RNA, 1 µl (2 U) of RNasH was added and incubated at 37° C. for 20 min. The resulting cDNA was then stored at −20° C. for further use.

XPO1A gene was amplified by PCR. The PCR reactions contained 0.5 µl of cDNA, 0.4 µl of dNTPs (10 mM), 1 µl of 10×Taq DNA polymerase buffer, 0.4 µl of each primer (SEQ ID NO 6 and SEQ ID NO 7), 0.1 µl of Taq DNA polymerase, and 6.7 µl of sterilized distilled water in a total volume of 9.5 µl. The conditions of PCR were as follows: 10 min at 94° C. followed by 40 cycles of denaturation, annealing and elongation at 94° C. for 30 sec, 65° C. for 30 sec and 68° C. for 90 sec, respectively, then additional extension at 68° C. for 7 min. The resulting PCR products were visualized on agarose gels stained with EtBr.

The PCR products can be purified by commercial kit or traditional purification methods for digestion and ligation.

DNA was digested with restriction enzymes following the manufacturers' recommendations. Briefly, DNA, buffer, distilled water and restriction enzyme were added and mixed well, and the reaction was performed at the proper temperature.

Ligation of DNA was performed using commercial kit (pGEM®-T and pGEM®-T Easy Vector Systems) according to the manufacturer's protocol. The pGEM®-T vector DNA, inserted DNA fragments, distilled water and ligation buffer were added and mixed well. Subsequently, $T_4$ ligase was added to the mixture, which was then incubated at the adequate temperature. The reaction was then terminated and the resulting plasmids were transformed into *E. coli* DH5α.

2. Transformation of *Agrobacterium tumefaciens*

The method described by Hofgen and Willmitzer (1988) was utilized for transformation of pCAMBIA1300-XPO1A into *Agrobacterium*.

A. Preparation of Competent Cells

Grow 200 ml culture of *Agrobacterium* strain GV3101 PMP90 overnight at 28° C. in LB medium with appropriate antibiotic. The logarithmically growing cells ($OD_{550}$ 0.5-0.8) were centrifuged for 10 min. The pellet was washed twice by sterilized Tris-EDTA buffer and resuspended in 20 ml fresh LB medium. Aliquots of 500 µl were frozen in liquid nitrogen and stored at −80° C.

B. Transformation

Stored competent cells were thawed on ice. Competent cells were mixed with 10 µl plasmid DNA. The cells were incubated 5 min on ice, 5 min in liquid nitrogen and 5 min at 37° C. After addition of 1 ml LB medium, the cells were shaken for 2-4 hours at 28° C. The cells were centrifuged and plated on LB-plates and incubated for 2 days at 28° C.

3. Transfection of Plant Cells

A. *Arabidopsis* was given as an example of transfection of plant cells. The seeds of *Arabidopsis* were grown in organic soil under 16 h:8 h light:dark cycles at 22° C. with light and 18° C. under dark conditions.

B. For transfection of pCAMBIA1300-XPO1A from *Agrobacterium* into *Arabidopsis*, *Agrobacterium*-mediated vacuum infiltration transformation was performed. Single colony of *Agrobacterium* was picked and grown in 5 ml of YEP medium containing appropriate antibiotics at 28° C. overnight. The small scale cultures were then diluted 50-fold into medium with appropriate antibiotics for large scale cultures. The cells were then harvested by centrifugation and resuspend in fresh AIM medium to an $OD_{600}$ of 0.6-1. AIM medium consists of half-strength MS salts, B5 vitamins, 0.01 mg/l benzylaminopurine (BA), 500 mg/l 2-(N-morpholino) ethanesulfonic acid (MES), 5% sucrose and 0.02% silwet-77.

The pots of *Arabidopsis* with 15-cm long rachis were selected and the siliques and bloomed flowers were removed. The plants were inverted and placed into the *Agrobacterium* suspension. Draw vacuum for 15 min using an oil pump. The pots were then removed from the *Agrobacterium* suspension and placed on their sides into a tray and incubated in dark. The next day, the pots were turned upright. The plants were grown under 16 h:8 h light:dark cycles at 22° C. with light and 18° C. under dark conditions. The seeds were harvested after approximately 45 days.

Although the present disclosure has been described in considerable detail with reference to certain embodiments thereof, other embodiments are possible. Therefore, their spirit and scope of the appended claims should not be limited to the description of the embodiments container herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claim.

What is claimed is:

1. A method of producing a transformed plant cell having basal thermotolerance by expressing an exogenous XPO1A protein, the method comprising:
   (a) introducing into a plurality of plant cells a polynucleotide that encodes the exogenous XPO1A protein comprising SEQ ID NO: 11;
   (b) expressing the exogenous XPO1A protein in the plant cells to form a plurality of transformed plant cells; and
   (c) selecting the transformed plant cell having basal thermotolerance under 37° C. for 3-4 days or 44° C. for 30 minutes.

2. The method of claim 1, wherein the polynucleotide comprises SEQ ID NO: 1.

3. The method of claim 2, wherein the polynucleotide sequence comprising SEQ ID NO: 1 is operably linked to a constitutive promoter or an inducible promoter.

4. The method of claim 1, wherein the polynucleotide comprises SEQ ID NO: 2 or SEQ ID NO: 3.

5. The method of claim 1, wherein the plant cell is from a plant that belongs to the family Brassicaceae or is from tomato.

6. The method of claim 1, wherein the plant cell is from a plant that belongs to the genus *Arabidopsis* or is from tomato.

7. The method of claim 1, wherein the recombinant vector is introduced into the plant cell by using a plasmid or a viral vehicle.

8. The method of claim 7, wherein the plasmid is a Ti-plasmid.

\* \* \* \* \*

```
                           SEQUENCE LISTING

<160> NUMBER OF SEQ ID NOS: 13

<210> SEQ ID NO 1
<211> LENGTH: 3228
<212> TYPE: DNA
<213> ORGANISM: Arabidopsis thaliana

<400> SEQUENCE: 1
atggcggctg agaagttaag ggacttgagc cagccgattg acgtcggtgt gctcgatgcc      60
actgttgcgg ccttctttgt taccggatct aaagaagaga gagctgctgc ggaccagatt     120
ttgcgggatt tgcaggctaa tccagatatg tggcttcaag ttgtccacat tctacaaaat     180
acaaacagct tggataccaa gttctttgct ctgcaggttc tagaaggtgt tataaagtat     240
agatggaatg cactgcctgt tgaacaacga gatggaatga aaaattacat ctcagaggtt     300
attgtacagc tctcgagtaa tgaagcatct ttcagatcag aaaggctcta tgtcaacaag     360
ctaaatgtca ttttggtcca gatcgtgaaa catgattggc cggcaaagtg gacaagcttc     420
attcctgatc tagttgcagc tgctaaaact agcgaaacta tctgcgaaaa ttgcatggcc     480
attttgaaac tcctaagtga agaggttttt gatttctcaa gaggagaaat gactcagcag     540
aagattaaag agctgaaaca atctctaaac agtgagttta aactcattca tgagttatgc     600
ctatatgtcc tctcagcttc tcaaagacag gatcttatac gtgcaacact gtctgcattg     660
catgcctatc tttcctggat tccattgggt tacattttg agtctacttt gcttgagacc      720
ctccttaaat tttttcctgt gccagcatat aggaacctca ctattcaatg tctgaccgag     780
gtcgcagctc ttaatttcgg ggacttctac aatgttcaat atgtcaaaat gtataccata     840
tttatagggc agctgcggat aattctccca ccgagtacaa agatccctga ggcatattcc     900
agtggaagtg gtgaagaaca agcatttatc cagaacctgg cactattttt cacttcccttt    960 ttcaagtttc atattcgagt cctagaatca acgccagaag ttgtctcttt gttactcgct    1020
ggtctagaat atctcattaa tatatcttat gttgacgaca ctgaagtatt taaggtttgt    1080
ttggactatt ggaactcgtt ggtgttggag ctatttgatg cgcatcataa ttctgataac    1140
cctgcagtaa gtgcaagcct gatgggtttg cagcctttcc ttcctggtat ggttgatggc    1200
cttggttctc aagtcatgca gcggcgtcaa ctttattctc acccaatgtc caaattaaga    1260
gggttaatga ttaaccgcat ggcgaagcct gaagaagtgc ttattgttga agatgaaaat    1320
gggaacatcg ttcgtgaaac catgaaggac aatgatgttc ttgtccaata taagataatg    1380
cgggagacat taatctacct ctcacacctt gaccatgatg ataccgagaa gcagatgttg    1440
aggaagctaa acaaacaatt aagtggggag gaatgggcat ggaacaattt gaacactttg    1500
tgctgggcta ttgggtctat ttccggatct atggcagaag atcaggaaaa caggttttg    1560
```

```
gtgatggtca ttcgtgattt gttgaattta tgtgaaatta ccaagggaaa agacaataaa    1620
gccgttattg caagcaacat catgtatgtc gttggccagt atccaagatt cttaagggcc    1680
cattggaagt ttttgaagac agttgtgaac aagttgtttg aattcatgca tgaaacacat    1740
cctggtgttc aggacatggc ctgtgataca ttccttgaaaa tagttcaaaa gtgcaagcga    1800
aaattcgtta ttgtacaggt tggagagaat gaaccatttg tatctgaact tctaacaggc    1860
cttgcaacaa ctgttcaaga tcttgagcct catcaaatac actcatttta tgaatcagtt    1920
ggtaatatga tccaagcaga atcagatcct cagaagagag atgaatatct ccagaggttg    1980
atggcactcc ccaaccagaa atgggcagaa atcataggac aggcacgcca cagtgtagaa    2040
ttcctcaagg atcaagttgt gatacgtaca gtgctaaaca tcctacagac taatactagt    2100
gctgctactt cactgggaac atacttctta tcccaaattt ccttgatttt cttggatatg    2160
ttgaatgtat acagaatgta cagtgagctt gtgtcaacca acattactga gggaggacca    2220
tatgcttcca agacatcttt tgtaaaactc ttaagatcgg ttaagaggga aacacttaag    2280
ctgatagaaa ccttttttaga caaagctgaa gaccagccac atagggaa acaatttgtg     2340 ccgccaatga tggaatcagt acttggtgac tatgcgagga atgtgcctga tgctagggaa    2400
tccgaagttc tttcactctt tgcaacgatt ataaacaagt acaaggcaac aatgttagac    2460
gacgtgcctc acatatttga agctgtattc cagtgtacat tggagatgat aactaagaac    2520
tttgaagatt atccagaaca ccgcctcaag tttttctcat tactccgtgc tattgctacg    2580
ttttgtttcc ctgccttgat aaagttatca agtccgcaac tgaagctagt gatggattca    2640
attatctggg catttagaca tactgagaga aatattgctg aaaccgggct taatcttttg    2700
cttgagatgc tgaaaaactt tcagcaatct gaattttgta atcaattcta ccggtcatac    2760
tttatgcaaa tcgagcaaga aatatttgcc gttttgaccg ataccttcca taagcctggc    2820
ttcaagctac atgtgttggt gctgcagcaa ctgttttgcc tgcctgagag cggtgctttg    2880
acagaaccct tgtgggatgc tacaaccgtt ccttacccgt atccggacaa cgttgcattt    2940
gttcgcgaat acaccattaa gctactgagc tcttcattcc caaacatgac tgcagcagag    3000
gtcacacaat ttgtgaatgg actatacgag tctagaaatg acccgtctgg atttaagaat    3060
aacattcgtg acttccttgt acagtctaag gagttttccg ctcaggataa caaagatctc    3120
tatgctgagg aagcagctgc acagagagag agagaacgtc aaagaatgct ttcaattcct    3180
gggcttattg ctcctaatga gattcaagac gagatggtgg actcataa                 3228
```

<210> SEQ ID NO 2
<211> LENGTH: 3576
<212> TYPE: DNA
<213> ORGANISM: Artificial sequence
<220> FEATURE:
<223> OTHER INFORMATION: polynucleotide sequence encoding XPO1A

<400> SEQUENCE: 2

```
tgagactttt caacaaaggg taatatccgg aaacctcctc ggattccatt gcccagctat     60
ctgtcacttt attgtgaaga tagtggaaaa ggaaggtggc tcctacaaat gccatcattg    120
cgataaagga aaggccatcg ttgaagatgc ctctgccgac agtggtccca agatggacc     180 cccacccacg aggagcatcg tggaaaaaga agacgttcca accacgtctt caaagcaagt    240
ggattgatgt gatatctcca ctgacgtaag ggatgacgca caatcccact atccttcgca    300
agacccttcc tctatataag gaagttcatt tcatttggag agaacacgat ggcggctgag    360
```

-continued

```
aagttaaggg acttgagcca gccgattgac gtcggtgtgc tcgatgccac tgttgcggcc    420
ttctttgtta ccggatctaa agaagagaga gctgctgcgg accagatttt gcgggatttg    480
caggctaatc cagatatgtg gcttcaagtt gtccacattc tacaaaatac aaacagcttg    540
gataccaagt tctttgctct gcaggttcta gaaggtgtta taaagtatag atggaatgca    600
ctgcctgttg aacaacgaga tggaatgaaa aattacatct cagaggttat tgtacagctc    660
tcgagtaatg aagcatcttt cagatcagaa aggctctatg tcaacaagct aaatgtcatt    720
ttggtccaga tcgtgaaaca tgattggccg gcaaagtgga caagcttcat tcctgatcta    780
gttgcagctg ctaaaactag cgaaactatc tgcgaaaatt gcatggccat tttgaaactc    840
ctaagtgaag aggttttga tttctcaaga ggagaaatga ctcagcagaa gattaaagag    900
ctgaaacaat ctctaaacag tgagtttaaa ctcattcatg agttatgcct atatgtcctc    960
tcagcttctc aaagacagga tcttatacgt gcaacactgt ctgcattgca tgcctatctt   1020
tcctggattc cattgggtta catttttgag tctactttgc ttgagcccct ccttaaattt   1080
tttcctgtgc cagcatatag gaacctcact attcaatgtc tgaccgaggt cgcagctctt   1140
aatttcgggg acttctacaa tgttcaatat gtcaaaatgt ataccatatt tatagggcag   1200
ctgcggataa ttctcccacc gagtacaaag atccctgagg catattccag tggaagtggt   1260
gaagaacaag catttatcca gaacctggca ctattttca cttcctttt caagtttcat   1320 attcgagtcc tagaatcaac gccagaagtt gtctctttgt tactcgctgg tctagaatat   1380
ctcattaata tatcttatgt tgacgacact gaagtattta aggtttgttt ggactattgg   1440
aactcgttgg tgttggagct atttgatgcg catcataatt ctgataaccc tgcagtaagt   1500
gcaagcctga tgggtttgca gccttttcctt cctggtatgg ttgatggcct tggttctcaa   1560
gtcatgcagc ggcgtcaact ttattctcac ccaatgtcca aattaagagg gttaatgatt   1620
aaccgcatgg cgaagcctga agaagtgctt attgttgaag atgaaaatgg gaacatcgtt   1680
cgtgaaacca tgaaggacaa tgatgttctt gtccaatata agataatgcg ggagacatta   1740
atctacctct cacaccttga ccatgatgat accgagaagc agatgttgag gaagctaaac   1800
aaacaattaa gtggggagga atgggcatgg aacaatttga acactttgtg ctgggctatt   1860
gggtctattt ccggatctat ggcagaagat caggaaaaca ggttttggt gatggtcatt   1920 cgtgatttgt tgaattttatg tgaaattacc aaggaaaag acaataaagc cgttattgca   1980
agcaacatca tgtatgtcgt tggccagtat ccaagattct taagggccca ttggaagtttt   2040 ttgaagacag ttgtgaacaa gttgttttgaa ttcatgcatg aaacacatcc tggtgttcag   2100
gacatggcct gtgatacatt cttgaaaata gttcaaaagt gcaagcgaaa attcgttatt   2160
gtacaggttg gagagaatga accatttgta tctgaacttc taacaggcct tgcaacaact   2220
gttcaagatc ttgagcctca tcaaatacac tcattttatg aatcagttgg taatatgatc   2280
caagcagaat cagatcctca gaagagagat gaatatctcc agaggttgat ggcactcccc   2340
aaccagaaat gggcagaaat cataggacag gcacgccaca gtgtagaatt cctcaaggat   2400
caagttgtga tacgtacagt gctaaacatc ctacagacta atactagtgc tgctacttca   2460
ctgggaacat acttcttatc ccaaatttcc ttgattttct tggatatgtt gaatgtatac   2520
agaatgtaca gtgagcttgt gtcaaccaac attactgagg gaggaccata tgcttccaag   2580
acatcttttg taaaactctt aagatcggtt aagagggaaa cacttaagct gatagaaacc   2640
tttttagaca aagctgaaga ccagccacac atagggaaac aatttgtgcc gccaatgatg   2700
gaatcagtac ttggtgacta tgcgaggaat gtgcctgatg ctagggaatc cgaagttctt   2760
```

-continued

| | |
|---|---|
| tcactctttg caacgattat aaacaagtac aaggcaacaa tgttagacga cgtgcctcac | 2820 |
| atatttgaag ctgtattcca gtgtacattg gagatgataa ctaagaactt tgaagattat | 2880 |
| ccagaacacc gcctcaagtt tttctcatta ctccgtgcta ttgctacgtt ttgtttccct | 2940 |
| gccttgataa agttatcaag tccgcaactg aagctagtga tggattcaat tatctgggca | 3000 |
| tttagacata ctgagagaaa tattgctgaa accgggctta atcttttgct tgagatgctg | 3060 |
| aaaaactttc agcaatctga attttgtaat caattctacc ggtcatactt tatgcaaatc | 3120 |
| gagcaagaaa tatttgccgt tttgaccgat accttccata agcctggctt caagctacat | 3180 |
| gtgttggtgc tgcagcaact gttttgcctg cctgagagcg gtgctttgac agaacccttg | 3240 |
| tgggatgcta caaccgttcc ttacccgtat ccggacaacg ttgcatttgt tcgcgaatac | 3300 |
| accattaagc tactgagctc ttcattccca aacatgactg cagcagaggt cacacaattt | 3360 |
| gtgaatggac tatacgagtc tagaaatgac ccgtctggat ttaagaataa cattcgtgac | 3420 |
| ttccttgtac agtctaagga gttttccgct caggataaca aagatctcta tgctgaggaa | 3480 |
| gcagctgcac agagagagag agaacgtcaa agaatgcttt caattcctgg gcttattgct | 3540 |
| cctaatgaga ttcaagacga gatggtggac tcataa | 3576 |

<210> SEQ ID NO 3
<211> LENGTH: 3483
<212> TYPE: DNA
<213> ORGANISM: Artificial sequence
<220> FEATURE:
<223> OTHER INFORMATION: polynucleotide sequence encoding XPO1A

<400> SEQUENCE: 3

| | |
|---|---|
| tatgcgggat agttccgacc taggattgga tgcatgcgga accgcacgag ggcggggcgg | 60 |
| aaattgacac accactcctc tccacgcacc gttcaagagg tacgcgtata gagccgtata | 120 |
| gagcagagac ggagcacttt ctggtactgt ccgcacggga tgtccgcacg gagagccaca | 180 |
| aacgagcggg gccccgtacg tgctctccta ccccaggatc gcatcccgc atagctgaac | 240 |
| atctatataa ctgcaatggc ggctgagaag ttaagggact tgagccagcc gattgacgtc | 300 |
| ggtgtgctcg atgccactgt tgcggccttc tttgttaccg gatctaaaga agagagagct | 360 |
| gctgcggacc agattttgcg ggatttgcag gctaatccag atatgtggct tcaagttgtc | 420 |
| cacattctac aaaatacaaa cagcttggat accaagttct tgctctgca ggttctagaa | 480 |
| ggtgttataa agtatagatg gaatgcactg cctgttgaac aacgagatgg aatgaaaaat | 540 |
| tacatctcag aggttattgt acagctctcg agtaatgaag catctttcag atcagaaagg | 600 |
| ctctatgtca caagctaaa tgtcattttg gtccagatcg tgaaacatga ttggccggca | 660 |
| aagtggacaa gcttcattcc tgatctagtt gcagctgcta aaactagcga aactatctgc | 720 |
| gaaaattgca tggccatttt gaaactccta agtgaagagg ttttttgattt ctcaagagga | 780 |
| gaaatgactc agcagaagat taagagctg aaacaatctc taaacagtga gtttaaactc | 840 |
| attcatgagt tatgcctata tgtcctctca gcttctcaaa gacaggatct tatacgtgca | 900 |
| acactgtctg cattgcatgc ctatctttcc tggattccat gggttacat ttttgagtct | 960 |
| actttgcttg agaccctcct taaatttttt cctgtgccag catataggaa cctcactatt | 1020 |
| caatgtctga ccgaggtcgc agctcttaat ttcggggact tctacaatgt tcaatatgtc | 1080 |
| aaaatgtata ccatatttat agggcagctg cggataattc tcccaccgag tacaaagatc | 1140 |
| cctgaggcat attccagtgg aagtggtgaa gaacaagcat ttatccagaa cctggcacta | 1200 |

```
tttttcactt cctttttcaa gtttcatatt cgagtcctag aatcaacgcc agaagttgtc    1260
tctttgttac tcgctggtct agaatatctc attaatatat cttatgttga cgacactgaa    1320
gtatttaagg tttgtttgga ctattggaac tcgttggtgt tggagctatt tgatgcgcat    1380
cataattctg ataaccctgc agtaagtgca agcctgatgg gtttgcagcc tttccttcct    1440
ggtatggttg atggccttgg ttctcaagtc atgcagcggc gtcaacttta ttctcaccca    1500
atgtccaaat taagagggtt aatgattaac cgcatggcga agcctgaaga agtgcttatt    1560
gttgaagatg aaaatgggaa catcgttcgt gaaaccatga aggacaatga tgttcttgtc    1620
caatataaga taatgcggga gacattaatc tacctctcac accttgacca tgatgatacc    1680
gagaagcaga tgttgaggaa gctaaacaaa caattaagtg gggaggaatg ggcatggaac    1740
aatttgaaca ctttgtgctg ggctattggg tctatttccg gatctatggc agaagatcag    1800
gaaaacaggt ttttggtgat ggtcattcgt gatttgttga atttatgtga aattaccaag    1860
ggaaaagaca ataaagccgt tattgcaagc aacatcatgt atgtcgttgg ccagtatcca    1920
agattcttaa gggcccattg gaagttttg aagacagttg tgaacaagtt gtttgaattc    1980
atgcatgaaa cacatcctgg tgttcaggac atggcctgtg atacattctt gaaaatagtt    2040
caaaagtgca agcgaaaatt cgttattgta caggttggag agaatgaacc atttgtatct    2100
gaacttctaa caggccttgc aacaactgtt caagatcttg agcctcatca aatacactca    2160
ttttatgaat cagttggtaa tatgatccaa gcagaatcag atcctcagaa gagagatgaa    2220
tatctccaga ggttgatggc actccccaac cagaaatggg cagaaatcat aggacaggca    2280
cgccacagtg tagaattcct caaggatcaa gttgtgatac gtacagtgct aaacatccta    2340
cagactaata ctagtgctgc tacttcactg ggaacatact tcttatccca aatttccttg    2400
attttcttgg atatgttgaa tgtatacaga atgtacagtg agcttgtgtc aaccaacatt    2460
actgagggag gaccatatgc ttccaagaca tcttttgtaa aactcttaag atcggttaag    2520
agggaaacac ttaagctgat agaaaccttt ttagacaaag ctgaagacca gccacacata    2580
gggaaacaat ttgtgccgcc aatgatggaa tcagtacttg gtgactatgc gaggaatgtg    2640
cctgatgcta gggaatccga agttctttca ctctttgcaa cgattataaa caagtacaag    2700
gcaacaatgt tagacgacgt gcctcacata tttgaagctg tattccagtg tacattggag    2760
atgataacta agaactttga agattatcca gaacaccgcc tcaagttttt ctcattactc    2820
cgtgctattg ctacgttttg tttccctgcc ttgataaagt tatcaagtcc gcaactgaag    2880
ctagtgatgg attcaattat ctgggcattt agacatactg agagaaatat tgctgaaacc    2940
gggcttaatc ttttgcttga gatgctgaaa aactttcagc aatctgaatt ttgtaatcaa    3000
ttctaccggt catactttat gcaaatcgag caagaaatat ttgccgtttt gaccgatacc    3060
ttccataagc ctggcttcaa gctacatgtg ttggtgctgc agcaactgtt ttgcctgcct    3120
gagagcggtg ctttgacaga acccttgtgg gatgctacaa ccgttcctta cccgtatccg    3180
gacaacgttg catttgttcg cgaatacacc attaagctac tgagctcttc attcccaaac    3240
atgactgcag cagaggtcac acaatttgtg aatggactat acgagtctag aaatgacccg    3300
tctggattta agaataacat tcgtgacttc cttgtacagt ctaaggagtt ttccgctcag    3360
gataacaaag atctctatgc tgaggaagca gctgcacaga gagagagaga acgtcaaaga    3420
atgctttcaa ttcctgggct tattgctcct aatgagattc aagacgagat ggtggactca    3480
taa                                                                  3483
```

```
<210> SEQ ID NO 4
<211> LENGTH: 27
<212> TYPE: DNA
<213> ORGANISM: Artificial sequence
<220> FEATURE:
<223> OTHER INFORMATION: forward primer used to amplify partial XPO1A
      cDNA by semiquantitative RT-PCR

<400> SEQUENCE: 4
gggcagctgc ggataattct cccaccg                                          27

<210> SEQ ID NO 5
<211> LENGTH: 25
<212> TYPE: DNA
<213> ORGANISM: Artificial sequence
<220> FEATURE:
<223> OTHER INFORMATION: reversed primer used to amplify partial XPO1A
      cDNA by semiquantitative RT-PCR

<400> SEQUENCE: 5
gacgccgctg catgacttga gaacc                                            25

<210> SEQ ID NO 6
<211> LENGTH: 31
<212> TYPE: DNA
<213> ORGANISM: Artificial sequence
<220> FEATURE:
<223> OTHER INFORMATION: forward primer used to amplify XPO1A gene by
      PCR

<400> SEQUENCE: 6
catgccatgg atggcggctg agaagttaag g                                     31

<210> SEQ ID NO 7
<211> LENGTH: 30
<212> TYPE: DNA
<213> ORGANISM: Artificial sequence
<220> FEATURE:
<223> OTHER INFORMATION: reversed primer used to amplify XPO1A gene by
      PCR

<400> SEQUENCE: 7
cgggatcctt gatgaggctc aagatcttga                                       30

<210> SEQ ID NO 8
<211> LENGTH: 348
<212> TYPE: DNA
<213> ORGANISM: Artificial sequence
<220> FEATURE:
<223> OTHER INFORMATION: 35S promoter

<400> SEQUENCE: 8
tgagactttt caacaaaggg taatatccgg aaacctcctc ggattccatt gcccagctat      60
ctgtcacttt attgtgaaga tagtggaaaa ggaaggtggc tcctacaaat gccatcattg     120
cgataaagga aaggccatcg ttgaagatgc ctctgccgac agtggtccca agatggacc      180 cccacccacg aggagcatcg tggaaaaaga agacgttcca accacgtctt caaagcaagt     240
ggattgatgt gatatctcca ctgacgtaag ggatgacgca caatcccact atccttcgca     300
agacccttcc tctatataag gaagttcatt tcatttggag agaacacg                  348

<210> SEQ ID NO 9
<211> LENGTH: 262
<212> TYPE: DNA
<213> ORGANISM: Artificial sequence
<220> FEATURE:
```

<223> OTHER INFORMATION: terminater

<400> SEQUENCE: 9

| | | | | | |
|---|---|---|---|---|---|
| gatcgttcaa | acatttggca | ataaagtttc | ttaagattga | atcctgttgc | cggtcttgcg | 60 |
| atgattatca | tataatttct | gttgaattac | gttaagcatg | taataattaa | catgtaatgc | 120 |
| atgacgttat | ttatgagatg | ggtttttatg | attagagtcc | cgcaattata | catttaatac | 180 |
| gcgatagaaa | acaaaatata | gcgcgcaaac | taggataaat | tatcgcgcgc | ggtgtcatct | 240 |
| atgttactag | atcgaattcg | at | | | | 262 |

<210> SEQ ID NO 10
<211> LENGTH: 8956
<212> TYPE: DNA
<213> ORGANISM: Artificial sequence
<220> FEATURE:
<223> OTHER INFORMATION: pCAMBIA1300 sequence

<400> SEQUENCE: 10

| | | | | | |
|---|---|---|---|---|---|
| aattcgagct | cggtacccgg | ggatcctcta | gagtcgacct | gcaggcatgc | aagcttggca | 60 |
| ctggccgtcg | ttttacaacg | tcgtgactgg | gaaaaccctg | gcgttaccca | acttaatcgc | 120 |
| cttgcagcac | atcccccttt | cgccagctgg | cgtaatagcg | aagaggcccg | caccgatcgc | 180 |
| ccttcccaac | agttgcgcag | cctgaatggc | gaatgctaga | gcagcttgag | cttggatcag | 240 |
| attgtcgttt | cccgccttca | gtttaaacta | tcagtgtttg | acaggatata | ttggcgggta | 300 |
| aacctaagag | aaaagagcgt | ttattagaat | aacggatatt | taaaagggcg | tgaaaaggtt | 360 |
| tatccgttcg | tccatttgta | tgtgcatgcc | aaccacaggg | ttcccctcgg | gatcaaagta | 420 |
| ctttgatcca | acccctccgc | tgctatagtg | cagtcggctt | ctgacgttca | gtgcagccgt | 480 |
| cttctgaaaa | cgacatgtcg | cacaagtcct | aagttacgcg | acaggctgcc | gccctgccct | 540 |
| tttcctggcg | ttttcttgtc | gcgtgtttta | gtcgcataaa | gtagaatact | tgcgactaga | 600 |
| accggagaca | ttacgccatg | aacaagagcg | ccgccgctgg | cctgctgggc | tatgcccgcg | 660 |
| tcagcaccga | cgaccaggac | ttgaccaacc | aacgggccga | actgcacgcg | gccggctgca | 720 |
| ccaagctgtt | ttccgagaag | atcaccggca | ccaggcgcga | ccgcccggag | ctggccagga | 780 |
| tgcttgacca | cctacgccct | ggcgacgttg | tgacagtgac | caggctagac | cgcctggccc | 840 |
| gcagcacccg | cgacctactg | gacattgccg | agcgcatcca | ggaggccggc | gcgggcctgc | 900 |
| gtagcctggc | agagccgtgg | gccgacacca | ccacgccggc | cggccgcatg | gtgttgaccg | 960 |
| tgttcgccgg | cattgccgag | ttcgagcgtt | ccctaatcat | cgaccgcacc | cggagcgggc | 1020 |
| gcgaggccgc | caaggcccga | ggcgtgaagt | ttggcccccg | ccctaccctc | accccggcac | 1080 |
| agatcgcgca | cgcccgcgag | ctgatcgacc | aggaaggccg | caccgtgaaa | gaggcggctg | 1140 |
| cactgcttgg | cgtgcatcgc | tcgaccctgt | accgcgcact | tgagcgcagc | gaggaagtga | 1200 |
| cgcccaccga | ggccaggcgg | cgcggtgcct | tccgtgagga | cgcattgacc | gaggccgacg | 1260 |
| ccctggcggc | cgccgagaat | gaacgccaag | aggaacaagc | atgaaaccgc | accaggacgg | 1320 |
| ccaggacgaa | ccgttttttca | ttaccgaaga | gatcgaggcg | gagatgatcg | cggccgggta | 1380 |
| cgtgttcgag | ccgcccgcgc | acgtctcaac | cgtgcggctg | catgaaatcc | tggccggttt | 1440 |
| gtctgatgcc | aagctggcgg | cctggccggc | cagcttggcc | gctgaagaaa | ccgagcgccg | 1500 |
| ccgtctaaaa | aggtgatgtg | tatttgagta | aaacagcttg | cgtcatgcgg | tcgctgcgta | 1560 |
| tatgatgcga | tgagtaaata | aacaaatacg | caaggggaac | gcatgaaggt | tatcgctgta | 1620 |
| cttaaccaga | aaggcgggtc | aggcaagacg | accatcgcaa | cccatctagc | ccgcgccctg | 1680 |

```
caactcgccg gggccgatgt tctgttagtc gattccgatc cccagggcag tgcccgcgat    1740
tgggcggccg tgcgggaaga tcaaccgcta accgttgtcg gcatcgaccg cccgacgatt    1800
gaccgcgacg tgaaggccat cggccggcgc gacttcgtag tgatcgacgg agcgccccag    1860
gcggcggact tggctgtgtc cgcgatcaag gcagccgact tcgtgctgat tccggtgcag    1920
ccaagcccct tacgacatatg ggccaccgcc gacctggtgg agctggttaa gcagcgcatt    1980
gaggtcacgg atggaaggct acaagcgccc tttgtcgtgt cgcgggcgat caaaggcacg    2040
cgcatcggcg gtgaggttgc cgaggcgctg gccgggtacg agctgcccat tcttgagtcc    2100
cgtatcacgc agcgcgtgag ctacccaggc actgccgccg ccggcacaac cgttcttgaa    2160
tcagaacccg agggcgacgc tgcccgcgag gtccaggcgc tggccgctga aattaaatca    2220
aaactcattt gagttaatga ggtaaagaga aaatgagcaa aagcacaaac acgctaagtg    2280
ccggccgtcc gagcgcacgc agcagcaagg ctgcaacgtt ggccagcctg cagacacgc    2340
cagccatgaa gcgggtcaac tttcagttgc cggcggagga tcacaccaag ctgaagatgt    2400
acgcggtacg ccaaggcaag accattaccg agctgctatc tgaatacatc gcgcagctac    2460
cagagtaaat gagcaaatga ataaatgagt agatgaattt tagcggctaa aggaggcggc    2520
atggaaaatc aagaacaacc aggcaccgac gccgtggaat gccccatgtg tggaggaacg    2580
ggcggttggc caggcgtaag cggctgggtt gtctgccggc cctgcaatgg cactggaacc    2640
cccaagcccg aggaatcggc gtgacggtcg caaaccatcc ggcccggtac aaatcggcgc    2700
ggcgctgggt gatgacctgg tggagaagtt gaaggccgcg caggccgcca gcggcaacgc    2760
atcgaggcaa agcacgcccg cggtgaatcg tggcaagcgg ccgctgatcg aatccgcaaa    2820
gaatcccggc aaccgccggc agccggtgcg ccgtcgatta ggaagccgcc caagggcgac    2880
gagcaaccag attttttcgt tccgatgctc tatgacgtgg gcacccgcga tagtcgcagc    2940
atcatggacg tggccgtttt ccgtctgtcg aagcgtgacc gacgagctgg cgaggtgatc    3000
cgctacgagc ttccagacgg gcacgtagag gtttccgcag ggccggccgg catggccagt    3060
gtgtgggatt acgacctggt actgatggcg gtttcccatc taaccgaatc catgaaccga    3120
taccgggaag ggaagggaga caagcccggc cgcgtgttcc gtccacacgt tgcggacgta    3180
ctcaagttct gccggcgagc cgatggcgga aagcagaaag acgacctggt agaaacctgc    3240
attcggttaa acaccacgca cgttgccatg cagcgtacga agaaggccaa gaacggccgc    3300
ctggtgacgg tatccgaggg tgaagccttg attagccgct acaagatcgt aaagagcgaa    3360
accgggcggc cggagtacat cgagatcgag ctagctgatt ggatgtaccg cgagatcaca    3420
gaaggcaaga acccggacgt gctgacggtt cacccccgatt acttttttgat cgatcccggc    3480
atcggccgtt ttctctaccg cctggcacgc cgcgccgcag gcaaggcaga agccagatgg    3540
ttgttcaaga cgatctacga acgcagtggc agcgccggag agttcaagaa gttctgtttc    3600
accgtgcgca agctgatcgg gtcaaatgac ctgccggagt acgatttgaa ggaggaggcg    3660
gggcaggctg gcccgatcct agtcatgcgc taccgcaacc tgatcgaggg cgaagcatcc    3720
gccggttcct aatgtacgga gcagatgcta gggcaaattg ccctagcagg ggaaaaaggt    3780
cgaaaaggtc tctttcctgt ggatagcacg tacattggga acccaaagcc gtacattggg    3840
aaccggaacc cgtacattgg gaacccaaag ccgtacattg gaaccggtc acacatgtaa    3900
gtgactgata taaagagaaa aaaggcgat ttttccgcct aaaactcttt aaaacttatt    3960
aaaactctta aaacccgcct ggcctgtgca taactgtctg gccagcgcac agccgaagag    4020
```

```
ctgcaaaaag cgcctaccct tcggtcgctg cgctccctac gccccgccgc ttcgcgtcgg    4080
cctatcgcgg ccgctggccg ctcaaaaatg gctggcctac ggccaggcaa tctaccaggg    4140
cgcggacaag ccgcgccgtc gccactcgac cgccggcgcc cacatcaagg caccctgcct    4200
cgcgcgtttc ggtgatgacg gtgaaaacct ctgacacatg cagctcccgg agacggtcac    4260
agcttgtctg taagcggatg ccgggagcag acaagcccgt cagggcgcgt cagcgggtgt    4320
tggcgggtgt cggggcgcag ccatgaccca gtcacgtagc gatagcggag tgtatactgg    4380
cttaactatg cggcatcaga gcagattgta ctgagagtgc accatatgcg gtgtgaaata    4440
ccgcacagat gcgtaaggag aaaataccgc atcaggcgct cttccgcttc ctcgctcact    4500
gactcgctgc gctcggtcgt tcggctgcgg cgagcggtat cagctcactc aaaggcggta    4560
atacggttat ccacagaatc aggggataac gcaggaaaga acatgtgagc aaaaggccag    4620
caaaaggcca ggaaccgtaa aaaggccgcg ttgctggcgt ttttccatag gctccgcccc    4680
cctgacgagc atcacaaaaa tcgacgctca agtcagaggt ggcgaaaccc gacaggacta    4740
taaagatacc aggcgtttcc ccctggaagc tccctcgtgc gctctcctgt tccgaccctg    4800
ccgcttaccg gatacctgtc cgcctttctc ccttcgggaa gcgtggcgct ttctcatagc    4860
tcacgctgta ggtatctcag ttcggtgtag gtcgttcgct ccaagctggg ctgtgtgcac    4920
gaaccccccg ttcagcccga ccgctgcgcc ttatccggta actatcgtct tgagtccaac    4980
ccggtaagac acgacttatc gccactggca gcagccactg gtaacaggat tagcagagcg    5040
aggtatgtag gcggtgctac agagttcttg aagtggtggc ctaactacgg ctacactaga    5100
aggacagtat ttggtatctg cgctctgctg aagccagtta ccttcggaaa aagagttggt    5160
agctcttgat ccggcaaaca aaccaccgct ggtagcggtg gtttttttgt ttgcaagcag    5220
cagattacgc gcagaaaaaa aggatctcaa gaagatcctt tgatcttttc tacgggtct    5280 gacgctcagt ggaacgaaaa ctcacgttaa gggattttgg tcatgcattc taggtactaa    5340
aacaattcat ccagtaaaat ataatatttt attttctccc aatcaggctt gatccccagt    5400
aagtcaaaaa atagctcgac atactgttct tccccgatat cctccctgat cgaccggacg    5460
cagaaggcaa tgtcatacca cttgtccgcc ctgccgcttc tcccaagatc aataaagcca    5520
cttactttgc catctttcac aaagatgttg ctgtctccca ggtcgccgtg ggaaaagaca    5580
agttcctctt cgggcttttc cgtctttaaa aaatcataca gctcgcgcgg attttaaatg    5640
gacgtgtctt cttcccagtt ttcgcaatcc acatcggcca gatcgttatt cagtaagtaa    5700
tccaattcgg ctaagcggct gtctaagcta ttcgtatagg gacaatccga tatgtcgatg    5760
gagtgaaaga gcctgatgca ctccgcatac agctcgataa tcttttcagg gctttgttca    5820
tcttcatact cttccgagca aaggacgcca tcggcctcac tcatgagcag attgctccag    5880
ccatcatgcc gttcaaagtg caggaccttt ggaacaggca gctttccttc cagccatagc    5940
atcatgtcct tttcccgttc cacatcatag gtggtccctt tataccggct gtccgtcatt    6000
tttaaatata ggttttcatt ttctcccacc agcttatata ccttagcagg agacattcct    6060
tccgtatctt ttacgcagcg gtattttcg atcagttttt tcaattccgg tgatattctc    6120
attttagcca tttattattt ccttcctctt ttctacagta tttaaagata ccccaagaag    6180
ctaattataa caagacgaac tccaattcac tgttccttgc attctaaaac cttaaatacc    6240
agaaaacagc ttttttcaaag ttgttttcaa agttggcgta taacatagta tcgacggagc    6300
cgattttgaa accgcggtga tcacaggcag caacgctctg tcatcgttac aatcaacatg    6360
ctaccctccg cgagatcatc cgtgtttcaa acccggcagc ttagttgccg ttcttccgaa    6420
```

```
tagcatcggt aacatgagca aagtctgccg ccttacaacg gctctcccgc tgacgccgtc   6480
ccggactgat gggctgcctg tatcgagtgg tgattttgtg ccgagctgcc ggtcggggag   6540
ctgttggctg gctggtggca ggatatattg tggtgtaaac aaattgacgc ttagacaact   6600
taataacaca ttgcggacgt ttttaatgta ctgaattaac gccgaattaa ttcgggggat   6660
ctggatttta gtactggatt ttggttttag gaattagaaa ttttattgat agaagtattt   6720
tacaaataca atacatacta agggtttctt atatgctcaa cacatgagcg aaaccctata   6780
ggaaccctaa ttcccttatc tgggaactac tcacacatta ttatggagaa actcgagctt   6840
gtcgatcgac agatccggtc ggcatctact ctatttcttt gccctcggac gagtgctggg   6900
gcgtcggttt ccactatcgg cgagtacttc tacacagcca tcggtccaga cggccgcgct   6960
tctgcgggcg atttgtgtac gcccgacagt cccggctccg gatcggacga ttgcgtcgca   7020
tcgaccctgc gcccaagctg catcatcgaa attgccgtca accaagctct gatagagttg   7080
gtcaagacca atgcggagca tatacgcccg gagtcgtggc gatcctgcaa gctccggatg   7140
cctccgctcg aagtagcgcg tctgctgctc catacaagcc aaccacggcc tccagaagaa   7200
gatgttggcg acctcgtatt gggaatcccc gaacatcgcc tcgctccagt caatgaccgc   7260
tgttatgcgg ccattgtccg tcaggacatt gttggagccg aaatccgcgt gcacgaggtg   7320
ccggacttcg gggcagtcct cggcccaaag catcagctca tcgagagcct gcgcgacgga   7380
cgcactgacg gtgtcgtcca tcacagtttg ccagtgatac acatggggat cagcaatcgc   7440
gcatatgaaa tcacgccatg tagtgtattg accgattcct tgcggtccga atgggccgaa   7500
cccgctcgtc tggctaagat cggccgcagc gatcgcatcc atagcctccg cgaccggttg   7560
tagaacagcg ggcagttcgg tttcaggcag gtcttgcaac gtgacaccct gtgcacggcg   7620
ggagatgcaa taggtcaggc tctcgctaaa ctccccaatg tcaagcactt ccggaatcgg   7680
gagcgcggcc gatgcaaagt gccgataaac ataacgatct tgtagaaac catcggcgca   7740 gctatttacc cgcaggacat atccacgccc tcctacatcg aagctgaaag cacgagattc   7800
ttcgccctcc gagagctgca tcaggtcgga gacgctgtcg aacttttcga tcagaaactt   7860
ctcgacagac gtcgcggtga gttcaggctt tttcatatct cattgccccc cgggatctgc   7920
gaaagctcga gagagataga tttgtagaga gagactggtg atttcagcgt gtcctctcca   7980
aatgaaatga acttccttat atagaggaag gtcttgcgaa ggatagtggg attgtgcgtc   8040
atcccttacg tcagtggaga tatcacatca atccacttgc tttgaagacg tggttggaac   8100
gtcttctttt tccacgatgc tcctcgtggg tggggtccca tctttgggac cactgtcggc   8160
agaggcatct tgaacgatag ccttccttt atcgcaatga tggcatttgt aggtgccacc   8220
ttccttttct actgtccttt tgatgaagtg acagatagct gggcaatgga atccgaggag   8280
gtttcccgat attacccttt gttgaaaagt ctcaatagcc ctttggtctt ctgagactgt   8340
atctttgata ttcttggagt agacgagagt gtcgtgctcc accatgttat cacatcaatc   8400
cacttgcttt gaagacgtgg ttggaacgtc ttcttttcc acgatgctcc tcgtgggtgg   8460
gggtccatct ttgggaccac tgtcggcaga ggcatcttga acgatagcct tcctttatc   8520 gcaatgatgg catttgtagg tgccaccttc cttttctact gtccttttga tgaagtgaca   8580
gatagctggg caatggaatc cgaggaggtt tcccgatatt acccttgtt gaaaagtctc   8640 aatagccctt tggtcttctg agactgtatc tttgatattc ttggagtaga cgagagtgtc   8700
gtgctccacc atgttggcaa gctgctctag ccaatacgca aaccgcctct ccccgcgcgt   8760
```

-continued

```
tggccgattc attaatgcag ctggcacgac aggtttcccg actggaaagc gggcagtgag    8820
cgcaacgcaa ttaatgtgag ttagctcact cattaggcac cccaggcttt acactttatg    8880
cttccggctc gtatgttgtg tggaattgtg agcggataac aatttcacac aggaaacagc    8940
tatgaccatg attacg                                                    8956
```

<210> SEQ ID NO 11
<211> LENGTH: 1075
<212> TYPE: PRT
<213> ORGANISM: Artificial sequence
<220> FEATURE:
<223> OTHER INFORMATION: XPO1A protein sequence
<400> SEQUENCE: 11

```
Met Ala Ala Glu Lys Leu Arg Asp Leu Ser Gln Pro Ile Asp Val Gly
 1               5                  10                  15

Val Leu Asp Ala Thr Val Ala Ala Phe Phe Val Thr Gly Ser Lys Glu
            20                  25                  30

Glu Arg Ala Ala Ala Asp Gln Ile Leu Arg Asp Leu Gln Ala Asn Pro
        35                  40                  45

Asp Met Trp Leu Gln Val Val His Ile Leu Gln Asn Thr Asn Ser Leu
    50                  55                  60

Asp Thr Lys Phe Phe Ala Leu Gln Val Leu Glu Gly Val Ile Lys Tyr
65                  70                  75                  80

Arg Trp Asn Ala Leu Pro Val Glu Gln Arg Asp Gly Met Lys Asn Tyr
                85                  90                  95

Ile Ser Glu Val Ile Val Gln Leu Ser Ser Asn Glu Ala Ser Phe Arg
            100                 105                 110

Ser Glu Arg Leu Tyr Val Asn Lys Leu Asn Val Ile Leu Val Gln Ile
        115                 120                 125

Val Lys His Asp Trp Pro Ala Lys Trp Thr Ser Phe Ile Pro Asp Leu
    130                 135                 140

Val Ala Ala Ala Lys Thr Ser Glu Thr Ile Cys Glu Asn Cys Met Ala
145                 150                 155                 160

Ile Leu Lys Leu Leu Ser Glu Glu Val Phe Asp Phe Ser Arg Gly Glu
                165                 170                 175

Met Thr Gln Gln Lys Ile Lys Glu Leu Lys Gln Ser Leu Asn Ser Glu
            180                 185                 190

Phe Lys Leu Ile His Glu Leu Cys Leu Tyr Val Leu Ser Ala Ser Gln
        195                 200                 205

Arg Gln Asp Leu Ile Arg Ala Thr Leu Ser Ala Leu His Ala Tyr Leu
    210                 215                 220

Ser Trp Ile Pro Leu Gly Tyr Ile Phe Glu Ser Thr Leu Leu Glu Thr
225                 230                 235                 240

Leu Leu Lys Phe Phe Pro Val Pro Ala Tyr Arg Asn Leu Thr Ile Gln
                245                 250                 255

Cys Leu Thr Glu Val Ala Ala Leu Asn Phe Gly Asp Phe Tyr Asn Val
            260                 265                 270

Gln Tyr Val Lys Met Tyr Thr Ile Phe Ile Gly Gln Leu Arg Ile Ile
        275                 280                 285

Leu Pro Pro Ser Thr Lys Ile Pro Glu Ala Tyr Ser Ser Gly Ser Gly
    290                 295                 300

Glu Glu Gln Ala Phe Ile Gln Asn Leu Ala Leu Phe Phe Thr Ser Phe
305                 310                 315                 320

Phe Lys Phe His Ile Arg Val Leu Glu Ser Thr Pro Glu Val Val Ser
```

-continued

```
                325                 330                 335
Leu Leu Leu Ala Gly Leu Glu Tyr Leu Ile Asn Ile Ser Tyr Val Asp
            340                 345                 350
Asp Thr Glu Val Phe Lys Val Cys Leu Asp Tyr Trp Asn Ser Leu Val
        355                 360                 365
Leu Glu Leu Phe Asp Ala His His Asn Ser Asp Asn Pro Ala Val Ser
370                 375                 380
Ala Ser Leu Met Gly Leu Gln Pro Phe Leu Pro Gly Met Val Asp Gly
385                 390                 395                 400
Leu Gly Ser Gln Val Met Gln Arg Arg Gln Leu Tyr Ser His Pro Met
                405                 410                 415
Ser Lys Leu Arg Gly Leu Met Ile Asn Arg Met Ala Lys Pro Glu Glu
            420                 425                 430
Val Leu Ile Val Glu Asp Glu Asn Gly Asn Ile Val Arg Glu Thr Met
        435                 440                 445
Lys Asp Asn Asp Val Leu Val Gln Tyr Lys Ile Met Arg Glu Thr Leu
450                 455                 460
Ile Tyr Leu Ser His Leu Asp His Asp Thr Glu Lys Gln Met Leu
465                 470                 475                 480
Arg Lys Leu Asn Lys Gln Leu Ser Gly Glu Glu Trp Ala Trp Asn Asn
                485                 490                 495
Leu Asn Thr Leu Cys Trp Ala Ile Gly Ser Ile Ser Gly Ser Met Ala
            500                 505                 510
Glu Asp Gln Glu Asn Arg Phe Leu Val Met Val Ile Arg Asp Leu Leu
        515                 520                 525
Asn Leu Cys Glu Ile Thr Lys Gly Lys Asp Asn Lys Ala Val Ile Ala
530                 535                 540
Ser Asn Ile Met Tyr Val Val Gly Gln Tyr Pro Arg Phe Leu Arg Ala
545                 550                 555                 560
His Trp Lys Phe Leu Lys Thr Val Val Asn Lys Leu Phe Glu Phe Met
                565                 570                 575
His Glu Thr His Pro Gly Val Gln Asp Met Ala Cys Asp Thr Phe Leu
            580                 585                 590
Lys Ile Val Gln Lys Cys Lys Arg Lys Phe Val Ile Gln Val Gly
        595                 600                 605
Glu Asn Glu Pro Phe Val Ser Glu Leu Leu Thr Gly Leu Ala Thr Thr
610                 615                 620
Val Gln Asp Leu Glu Pro His Gln Ile His Ser Phe Tyr Glu Ser Val
625                 630                 635                 640
Gly Asn Met Ile Gln Ala Glu Ser Asp Pro Gln Lys Arg Asp Glu Tyr
                645                 650                 655
Leu Gln Arg Leu Met Ala Leu Pro Asn Gln Lys Trp Ala Glu Ile Ile
            660                 665                 670
Gly Gln Ala Arg His Ser Val Glu Phe Leu Lys Asp Gln Val Val Ile
        675                 680                 685
Arg Thr Val Leu Asn Ile Leu Gln Thr Asn Thr Ser Ala Ala Thr Ser
690                 695                 700
Leu Gly Thr Tyr Phe Leu Ser Gln Ile Ser Leu Ile Phe Leu Asp Met
705                 710                 715                 720
Leu Asn Val Tyr Arg Met Tyr Ser Glu Leu Val Ser Thr Asn Ile Thr
                725                 730                 735
Glu Gly Gly Pro Tyr Ala Ser Lys Thr Ser Phe Val Lys Leu Leu Arg
            740                 745                 750
```

Ser Val Lys Arg Glu Thr Leu Lys Leu Ile Glu Thr Phe Leu Asp Lys
    755                 760                 765

Ala Glu Asp Gln Pro His Ile Gly Lys Gln Phe Val Pro Pro Met Met
        770                 775                 780

Glu Ser Val Leu Gly Asp Tyr Ala Arg Asn Val Pro Asp Ala Arg Glu
785                 790                 795                 800

Ser Glu Val Leu Ser Leu Phe Ala Thr Ile Ile Asn Lys Tyr Lys Ala
                805                 810                 815

Thr Met Leu Asp Asp Val Pro His Ile Phe Glu Ala Val Phe Gln Cys
            820                 825                 830

Thr Leu Glu Met Ile Thr Lys Asn Phe Glu Asp Tyr Pro Glu His Arg
        835                 840                 845

Leu Lys Phe Phe Ser Leu Leu Arg Ala Ile Ala Thr Phe Cys Phe Pro
    850                 855                 860

Ala Leu Ile Lys Leu Ser Ser Pro Gln Leu Lys Leu Val Met Asp Ser
865                 870                 875                 880

Ile Ile Trp Ala Phe Arg His Thr Glu Arg Asn Ile Ala Glu Thr Gly
                885                 890                 895

Leu Asn Leu Leu Leu Glu Met Leu Lys Asn Phe Gln Gln Ser Glu Phe
            900                 905                 910

Cys Asn Gln Phe Tyr Arg Ser Tyr Phe Met Gln Ile Glu Gln Glu Ile
        915                 920                 925

Phe Ala Val Leu Thr Asp Thr Phe His Lys Pro Gly Phe Lys Leu His
    930                 935                 940

Val Leu Val Leu Gln Gln Leu Phe Cys Leu Pro Glu Ser Gly Ala Leu
945                 950                 955                 960

Thr Glu Pro Leu Trp Asp Ala Thr Thr Val Pro Tyr Pro Tyr Pro Asp
                965                 970                 975

Asn Val Ala Phe Val Arg Glu Tyr Thr Ile Lys Leu Leu Ser Ser Ser
            980                 985                 990

Phe Pro Asn Met Thr Ala Ala Glu Val Thr Gln Phe Val Asn Gly Leu
        995                 1000                1005

Tyr Glu Ser Arg Asn Asp Pro Ser Gly Phe Lys Asn Asn Ile Arg Asp
    1010                1015                1020

Phe Leu Val Gln Ser Lys Glu Phe Ser Ala Gln Asp Asn Lys Asp Leu
1025                1030                1035                1040

Tyr Ala Glu Glu Ala Ala Ala Gln Arg Glu Arg Glu Arg Gln Arg Met
                1045                1050                1055

Leu Ser Ile Pro Gly Leu Ile Ala Pro Asn Glu Ile Gln Asp Glu Met
            1060                1065                1070

Val Asp Ser
    1075

<210> SEQ ID NO 12
<211> LENGTH: 3228
<212> TYPE: DNA
<213> ORGANISM: Artificial sequence
<220> FEATURE:
<223> OTHER INFORMATION: polynucleotide sequence encoding HIT2

<400> SEQUENCE: 12
atggcggctg agaagttaag ggacttgagc cagccgattg acgtcggtgt gctcgatgcc      60
actgttgcgg ccttctttgt taccggatct aaagaagaga gagctgctgc ggaccagatt     120
ttgcgggatt tgcaggctaa tccagatatg tggcttcaag ttgtccacat tctacaaaat     180

```
acaaacagct tggataccaa gttctttgct ctgcaggttc tagaaggtgt tataaagtat    240
agatggaatg cactgcctgt tgaacaacga gatggaatga aaattacat ctcagaggtt     300 attgtacagc tctcgagtaa tgaagcatct ttcagatcag aaaggctcta tgtcaacaag    360
ctaaatgtca ttttggtcca gatcgtgaaa catgattggc cggcaaagtg acaagcttc     420 attcctgatc tagttgcagc tgctaaaact agcgaaacta tctgcgaaaa ttgcatggcc    480
attttgaaac tcctaagtga agaggttttt gatttctcaa gaggagaaat gactcagcag    540
aagattaaag agctgaaaca atctctaaac agtgagttta aactcattca tgagttatgc    600
ctatatgtcc tctcagcttc tcaaagacag gatcttatac gtgcaacact gtctgcattg    660
catgcctatc tttcctggat tccattgggt tacattttg agtctacttt gcttgagacc     720
ctccttaaat tttttcctgt gccagcatat aggaacctca ctattcaatg tctgaccgag    780
gtcgcagctc ttaatttcgg ggacttctac aatgttcaat atgtcaaaat gtataccata    840
tttatagggc agctgcggat aattctccca ccgagtacaa agatccctga ggcatattcc    900
agtggaagtg gtgaagaaca agcatttatc cagaacctgg cactatttt cacttccttt     960 ttcaagtttc atattcgagt cctagaatca acgccagaag ttgtctcttt gttactcgct   1020
ggtctagaat atctcattaa tatatcttat gttgacgaca ctgaagtatt taaggtttgt   1080
ttggactatt gaaactcgtt ggtgttggag ctatttgatg cgcatcataa ttctgataac   1140
cctgcagtaa gtgcaagcct gatgggtttg cagccttcc ttcctggtat ggttgatggc    1200
cttggttctc aagtcatgca gcggcgtcaa ctttattctc acccaatgtc caaattaaga   1260
gggttaatga ttaaccgcat ggcgaagcct gaagaagtgc ttattgttga agatgaaaat   1320
gggaacatcg ttcgtgaaac catgaaggac aatgatgttc ttgtccaata taagataatg   1380
cgggagacat taatctacct ctcacacctt gaccatgatg ataccgagaa gcagatgttg   1440
aggaagctaa acaaacaatt aagtggggag aatgggcat ggaacaattt gaacactttg     1500
tgctgggcta ttgggtctat ttccggatct atggcagaag atcaggaaaa caggttttg    1560 gtgatggtca ttcgtgattt gttgaattta tgtgaaatta ccaagggaaa agacaataaa   1620
gccgttattg caagcaacat catgtatgtc gttggccagt atccaagatt cttaagggcc   1680
cattggaagt ttttgaagac agttgtgaac aagttgtttg aattcatgca tgaaacacat   1740
cctggtgttc aggacatggc ctgtgataca ttcttgaaaa tagttcaaaa gtgcaagcga   1800
aaattcgtta ttgtacaggt tggagagaat gaaccatttg tatctgaact tctaacaggc   1860
cttgcaacaa ctgttcaaga tcttgagcct catcaaatac actcatttta tgaatcagtt   1920
ggtaatatga tccaagcaga atcagatcct cagaagagag atgaatatct ccagaggttg   1980
atggcactcc ccaaccagaa atgggcagaa atcataggac aggcacgcca cagtgtagaa   2040
ttcctcaagg atcaagttgt gatacgtaca gtgctaaaca tcctacagac taatactagt   2100
gctgctactt cactgggaac atacttctta tcccaaattt ccttgatttt cttggatatg   2160
ttgaatgtat acagaatgta cagtgagctt gtgtcaacca acattactga gggaggacca   2220
tatgcttcca agacatcttt tgtaaaactc ttaagatcgg ttaagaggga aacacttaag   2280
ctgatagaaa cctttttaga caaagctgaa gaccagccac acatagggaa acaatttgtg   2340
ccgccaatga tggaatcagt acttggtgac tatgcgagga atgtgcctga tgctagggaa   2400
tccgaagttc tttcactctt tgcaacgatt ataaacaagt acaaggcaac aatgttagac   2460
gacgtgcctc acatatttga agctgtattc cagtgtacat tggagatgat aactaagaac   2520
```

-continued

```
tttgaagatt atccagaaca ccgcctcaag ttttttctcat tactccgtgc tattgctacg    2580 ttttgttttcc ctgccttgat aaagttatca gtccgcaac tgaagctagt gatggattca     2640
attatctggg catttagaca tactgagaga aatattgctg aaaccgggct taatcttttg     2700
cttgagatgc tgaaaaactt tcagcaatct gaattttgta atcaattcta ccggtcatac    2760
tttatgcaaa tcgagcaaga aatatttgcc gttttgaccg ataccttcca taagcctggc    2820
ttcaagctac atgtgttggt gctgcagcaa ctgttttgcc tgcctgagag cggtgctttg    2880
acagaaccct tgtgggatgc tacaaccgtt ccttacccgt atccggacaa cgttgcattt    2940
gttcgcgaat acaccattaa gctactgagc tcttcattcc caaacatgac tgcagcagag    3000
gtcacacaat ttgtgaatgg actatacgag tctagaaatg acccgtctgg atttaagaat    3060
aacattcgtg acttccttgt acagtctaag gagttttccg ctcaggataa caaagatctc    3120
tatgctgagg aagcagctgc acagagagag agagaacgtc aaagaatgct ttcaattcct    3180
gggcttattg ctcctaatga gattcaagac gagatggtgg actcataa                 3228
```

<210> SEQ ID NO 13
<211> LENGTH: 363
<212> TYPE: PRT
<213> ORGANISM: Artificial sequence
<220> FEATURE:
<223> OTHER INFORMATION: HIT2 protein sequence

<400> SEQUENCE: 13

```
Met Ala Ala Glu Lys Leu Arg Asp Leu Ser Gln Pro Ile Asp Val Gly
 1               5                  10                  15

Val Leu Asp Ala Thr Val Ala Ala Phe Phe Val Thr Gly Ser Lys Glu
                20                  25                  30

Glu Arg Ala Ala Ala Asp Gln Ile Leu Arg Asp Leu Gln Ala Asn Pro
            35                  40                  45

Asp Met Trp Leu Gln Val Val His Ile Leu Gln Asn Thr Asn Ser Leu
        50                  55                  60

Asp Thr Lys Phe Phe Ala Leu Gln Val Leu Glu Gly Val Ile Lys Tyr
65                  70                  75                  80

Arg Trp Asn Ala Leu Pro Val Glu Gln Arg Asp Gly Met Lys Asn Tyr
                85                  90                  95

Ile Ser Glu Val Ile Val Gln Leu Ser Ser Asn Glu Ala Ser Phe Arg
            100                 105                 110

Ser Glu Arg Leu Tyr Val Asn Lys Leu Asn Val Ile Leu Val Gln Ile
        115                 120                 125

Val Lys His Asp Trp Pro Ala Lys Trp Thr Ser Phe Ile Pro Asp Leu
    130                 135                 140

Val Ala Ala Ala Lys Thr Ser Glu Thr Ile Cys Glu Asn Cys Met Ala
145                 150                 155                 160

Ile Leu Lys Leu Leu Ser Glu Glu Val Phe Asp Phe Ser Arg Gly Glu
                165                 170                 175

Met Thr Gln Gln Lys Ile Lys Glu Leu Lys Gln Ser Leu Asn Ser Glu
            180                 185                 190

Phe Lys Leu Ile His Glu Leu Cys Leu Tyr Val Leu Ser Ala Ser Gln
        195                 200                 205

Arg Gln Asp Leu Ile Arg Ala Thr Leu Ser Ala Leu His Ala Tyr Leu
    210                 215                 220

Ser Trp Ile Pro Leu Gly Tyr Ile Phe Glu Ser Thr Leu Leu Glu Thr
225                 230                 235                 240
```

-continued

```
Leu Leu Lys Phe Phe Pro Val Pro Ala Tyr Arg Asn Leu Thr Ile Gln
            245                 250                 255

Cys Leu Thr Glu Val Ala Ala Leu Asn Phe Gly Asp Phe Tyr Asn Val
            260                 265                 270

Gln Tyr Val Lys Met Tyr Thr Ile Phe Ile Gly Gln Leu Arg Ile Ile
            275                 280                 285

Leu Pro Pro Ser Thr Lys Ile Pro Glu Ala Tyr Ser Ser Gly Ser Gly
            290                 295                 300

Glu Glu Gln Ala Phe Ile Gln Asn Leu Ala Leu Phe Phe Thr Ser Phe
305                 310                 315                 320

Phe Lys Phe His Ile Arg Val Leu Glu Ser Thr Pro Glu Val Val Ser
            325                 330                 335

Leu Leu Leu Ala Gly Leu Glu Tyr Leu Ile Asn Ile Ser Tyr Val Asp
            340                 345                 350

Asp Thr Glu Val Phe Lys Val Cys Leu Asp Tyr
            355                 360
```